(12) United States Patent
Karino

(10) Patent No.: US 12,082,769 B2
(45) Date of Patent: Sep. 10, 2024

(54) ENDOSCOPE SYSTEM

(71) Applicant: FUJIFILM Corporation, Tokyo (JP)

(72) Inventor: Takatoshi Karino, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 773 days.

(21) Appl. No.: 17/164,695

(22) Filed: Feb. 1, 2021

(65) Prior Publication Data

US 2021/0153730 A1 May 27, 2021

Related U.S. Application Data

(63) Continuation of application No. PCT/JP2019/031431, filed on Aug. 8, 2019.

(30) Foreign Application Priority Data

Aug. 17, 2018 (JP) ................. 2018-153732

(51) Int. Cl.
*A61B 1/00* (2006.01)
*A61B 1/045* (2006.01)
(Continued)

(52) U.S. Cl.
CPC .. *A61B 1/000094* (2022.02); *A61B 1/000096* (2022.02); *A61B 1/045* (2013.01);
(Continued)

(58) Field of Classification Search
CPC ........ A61B 1/000094; A61B 1/000096; A61B 1/045; A61B 1/0655; A61B 1/0661;
(Continued)

(56) References Cited

U.S. PATENT DOCUMENTS 5,971,918 A * 10/1999 Zanger ................. A61B 5/0084
600/181
7,376,155 B2 * 5/2008 Ahn ....................... G06F 16/40
370/522

(Continued)

FOREIGN PATENT DOCUMENTS

| CN | 106999076 | 8/2017 |
|---|---|---|
| CN | 107708521 | 2/2018 |

(Continued)

OTHER PUBLICATIONS

"Office Action of China Counterpart Application", issued on Jun. 10, 2023, with English translation thereof, pp. 1-10.

(Continued)

*Primary Examiner* — Jerome Grant, II
(74) *Attorney, Agent, or Firm* — JCIPRNET

(57) ABSTRACT

An endoscope system includes an identification unit that identifies the type of an image obtained by image capturing of a photographic subject, a recognition unit that performs a recognition process of recognizing the photographic subject by using the image, and a notification unit that gives a notification of whether the recognition process functions for the image of a specific type identified by the identification unit. The identification unit identifies the type of the image by determining an operation mode, the model of an endoscope used in image capturing of the photographic subject, or whether or not a drug is administered to the photographic subject.

35 Claims, 17 Drawing Sheets

(51) Int. Cl.
*A61B 1/06* (2006.01)
*G06V 10/141* (2022.01)
*G06V 10/147* (2022.01)
*G06V 10/25* (2022.01)

(52) U.S. Cl.
CPC .......... *A61B 1/0655* (2022.02); *A61B 1/0661* (2013.01); *G06V 10/141* (2022.01); *G06V 10/147* (2022.01); *G06V 10/25* (2022.01)

(58) Field of Classification Search
CPC .. A61B 1/0005; A61B 1/0638; G06V 10/141; G06V 10/147; G06V 10/25; G06V 2201/031; G06T 2207/10068; G06T 2207/30096; G06T 7/0012
USPC ........................................................ 382/128
See application file for complete search history.

(56) References Cited

U.S. PATENT DOCUMENTS

| | | | |
|---|---|---|---|
| 8,313,426 | B2 | 11/2012 | Nakaoka et al. |
| 9,675,287 | B2 | 6/2017 | Saito |
| 2005/0049458 | A1 | 3/2005 | Honda et al. |
| 2006/0155166 | A1 | 7/2006 | Takahashi et al. |
| 2008/0039692 | A1 | 2/2008 | Hirakawa |
| 2010/0004505 | A1 | 1/2010 | Umemoto et al. |
| 2010/0194871 | A1 | 8/2010 | Komukai |
| 2012/0053421 | A1* | 3/2012 | Yoshida ............. G02B 23/2469 29/428 |
| 2014/0100431 | A1* | 4/2014 | Curcillo ............. A61B 17/3421 600/249 |
| 2016/0157787 | A1 | 6/2016 | Merritt et al. |
| 2016/0174848 | A1 | 6/2016 | Ammar |
| 2018/0114319 | A1 | 4/2018 | Kono et al. |
| 2018/0214009 | A1* | 8/2018 | Endo ...................... A61B 1/063 |
| 2019/0311476 | A1 | 10/2019 | Hayami et al. |
| 2022/0000427 | A1 | 1/2022 | Merritt et al. |

FOREIGN PATENT DOCUMENTS

| | | | | |
|---|---|---|---|---|
| EP | 3633987 | | 4/2020 | |
| JP | S63259614 | | 10/1988 | |
| JP | H03277340 | | 12/1991 | |
| JP | H07250812 | | 10/1995 | |
| JP | 2005006974 | | 1/2005 | |
| JP | 2005073799 | | 3/2005 | |
| JP | 2005124756 | | 5/2005 | |
| JP | 2006218138 | | 8/2006 | |
| JP | 2006271870 | | 10/2006 | |
| JP | 2007330405 | | 12/2007 | |
| JP | 2008161550 | | 7/2008 | |
| JP | 2008245840 | | 10/2008 | |
| JP | 2010172530 X | | 8/2010 | |
| JP | 2010172673 | | 8/2010 | |
| JP | 2011104199 | * | 6/2011 | ......... A61B 1/00188 |
| JP | 2012152332 | | 8/2012 | |
| JP | 2015177961 | | 10/2015 | |
| JP | 2017536213 | | 12/2017 | |
| JP | 2018051364 | | 4/2018 | |
| WO | 2017002184 | | 1/2017 | |
| WO | 2018105063 | | 6/2018 | |

OTHER PUBLICATIONS

"International Search Report (Form PCT/ISA/210) of PCT/JP2019/031431," mailed on May 11, 2019, with English translation thereof, pp. 1-5.

"Written Opinion of the International Searching Authority (Form PCT/ISA/237) of PCT/JP2019/031431," mailed on May 11, 2019, with English translation thereof, pp. 1-14.

"Office Action of Japan Counterpart Application", issued on Feb. 7, 2023, with English translation thereof, pp. 1-12.

"Office Action of Japan Counterpart Application", issued on Apr. 5, 2022, with English translation thereof, p1-p12.

"Search Report of Europe Counterpart Application", issued on Sep. 6, 2021, p1-p7.

"Office Action of Japan Counterpart Application", issued on Sep. 13, 2022, with English translation thereof, pp. 1-11.

"Office Action of China Counterpart Application", issued on Feb. 29, 2024, with English translation thereof, p1-p9.

"Office Action of Europe Counterpart Application", issued on Feb. 22, 2024, p1-p4.

Office Action of Japan Counterpart Application, with English translation thereof, issued on Oct. 10, 2022, pp. 1-12.

"Office Action of Japan Counterpart Application", issued on Jan. 23, 2024, with English translation thereof, pp. 1-16.

"Office Action of Japan Counterpart Application", issued on Apr. 30, 2024, with English translation thereof, p. 1-21.

* cited by examiner

| | | OPERATION MODE, etc. | |
|---|---|---|---|
| | | RECOGNITION PROCESS: POSSIBLE | RECOGNITION PROCESS: NOT POSSIBLE |
| RECOGNITION PROCESS | ENABLED | FIRST NOTIFICATION FORM | THIRD NOTIFICATION FORM |
| | DISABLED | SECOND NOTIFICATION FORM | FOURTH NOTIFICATION FORM |

ENDOSCOPE SYSTEM

CROSS-REFERENCE TO RELATED APPLICATIONS

This application is a Continuation of PCT International Application No. PCT/JP2019/031431 filed on 8 Aug. 2019, which claims priority under 35 U.S.C. § 119(a) to Japanese Patent Application No. 2018-153732 filed on 17 Aug. 2018. The above application is hereby expressly incorporated by reference, in its entirety, into the present application.

BACKGROUND OF THE INVENTION

1. Field of the Invention

The present invention relates to an endoscope system that performs a recognition process for a photographic subject using an image captured by using an endoscope.

2. Description of the Related Art

In the medical field, endoscope systems that include a light source device, an endoscope, and a processor device are in widespread use. The light source device generates illumination light. The endoscope captures an image of a photographic subject by using an image sensor. The processor device generates an image and performs other image processing and so on.

Endoscope systems may not only capture an image of a photographic subject for observation but also have additional functions. For example, an endoscope system that has an "input mode" in which the position and orientation of a treatment tool are controlled by using a touch panel is known (JP2008-245840A (corresponding to US2010/0004505A1)). In the endoscope system described in JP2008-245840A, the state of the input mode is displayed on a screen. An endoscope system that has a function of displaying on a screen an image representing the bending state of a tip part of an endoscope and a character string for notification of, for example, completion of calibration to thereby give a notification of, for example, a system error is known (JP2007-330405A). In addition, an endoscope system that displays on a screen the ON state or the OFF state of a foot switch (JP2005-073799A (corresponding to US2005/0049458A1)), an endoscope system that displays on a screen a mark indicating that air supply is ongoing (JP1991-277340A (JP-H03-277340A)), and an endoscope system that displays on a screen the ON state or the OFF state of image recording (JP1988-259614A (JP-S63-259614A)) are known.

In addition, currently, an endoscope system that supports diagnoses by, for example, calculating biological function information using a captured image of a photographic subject is known (JP2018-051364A).

SUMMARY OF THE INVENTION

In a case where a medical image, such as an image captured by using an endoscope (hereinafter referred to as an endoscopic image), is used to recognize a photographic subject having specific characteristics or part of the photographic subject, thereby obtaining information for supporting a diagnosis (hereinafter referred to as diagnosis support information), it is necessary to use a medical image that is captured under specific conditions such that a recognition process can function for the medical image. When a medical image for which a recognition process does not function is used, even when the result of the recognition process is obtained, the result of the recognition process may be inaccurate.

It is not necessarily the case that a medical image for which a recognition process can function is always obtained. Accordingly, an inaccurate result of the recognition process or diagnosis support information obtained by, for example, calculation using an inaccurate result of the recognition process may hinder observation or a diagnosis of the photographic subject. For example, in an endoscope system that has a plurality of observation modes in which different types of illumination light are used in image capturing, a highly accurate result of a recognition process is obtained for an endoscopic image that is obtained in a specific observation mode, but the accuracy of the recognition process may be low in a case where an endoscopic image obtained in another observation mode is used.

In order not to provide, for example, an inaccurate result of a recognition process as described above, the recognition process can be prevented from being performed unless a medical image for which the recognition process can function is obtained. However, when the recognition process is simply prohibited from being performed, a doctor or the like, who is a user, may incorrectly recognize the result of performing the recognition process or the result of not performing the recognition process. For example, in a case of using, for example, an apparatus that performs a recognition process for detecting a potential lesion, when the recognition process is simply prohibited from being performed, a doctor or the like who is using the apparatus may incorrectly recognize that the recognition process is performed and a potential lesion is not detected as a result of the recognition process. That is, a doctor or the like may unable to determine whether the result of the recognition process is not displayed because the recognition process is not performed or the result of the recognition process is not displayed because the recognition process is performed and a recognition target is not detected as a result of the recognition process.

An object of the present invention is to provide an endoscope system that at least prevents incorrect recognition of the result of performing a recognition process and the result of not performing the recognition process.

An endoscope system according to the present invention includes: an identification unit that identifies a type of an image obtained by image capturing of a photographic subject; a recognition unit that performs a recognition process of recognizing the photographic subject by using the image; and a notification unit that gives a notification of whether the recognition process functions for the image of a specific type identified by the identification unit.

Preferably, the identification unit identifies the type of the image by determining an operation mode, a model of an endoscope used in image capturing of the photographic subject, or whether or not a drug is administered to the photographic subject.

Preferably, the identification unit identifies the type of the image by determining a type of illumination light used in image capturing, whether or not an optical enlargement process is performed, or the operation mode that is determined on the basis of whether or not image processing is performed.

Preferably, the notification unit gives the notification of whether the recognition process functions at least in a case where the type of the image switches.

Preferably, the notification unit gives the notification of whether the recognition process functions in a form that differs depending on whether the recognition unit is active or the recognition unit is inactive.

Preferably, the recognition unit is automatically activated in a case where the type of the image is a type for which the recognition process functions, and the recognition unit is automatically inactivated in a case where the type of the image is a type for which the recognition process does not function.

Preferably, the recognition unit recognizes presence or absence of a lesion or a potential lesion of the photographic subject.

Preferably, the recognition unit recognizes a type or a degree of progression of a lesion or a potential lesion of the photographic subject.

Preferably, the recognition unit is an artificial intelligence having a learning function.

Preferably, in a case where the endoscope system has a plurality of recognition units that function for different types of images, each of the plurality of recognition units being the recognition unit, the notification unit gives, for each of the recognition units, the notification of whether the recognition process functions.

According to the present invention, it is possible to provide an endoscope system that prevents incorrect recognition of the result of performing a recognition process and the result of not performing the recognition process.

DESCRIPTION OF THE PREFERRED EMBODIMENTS

First Embodiment

Figure 1:
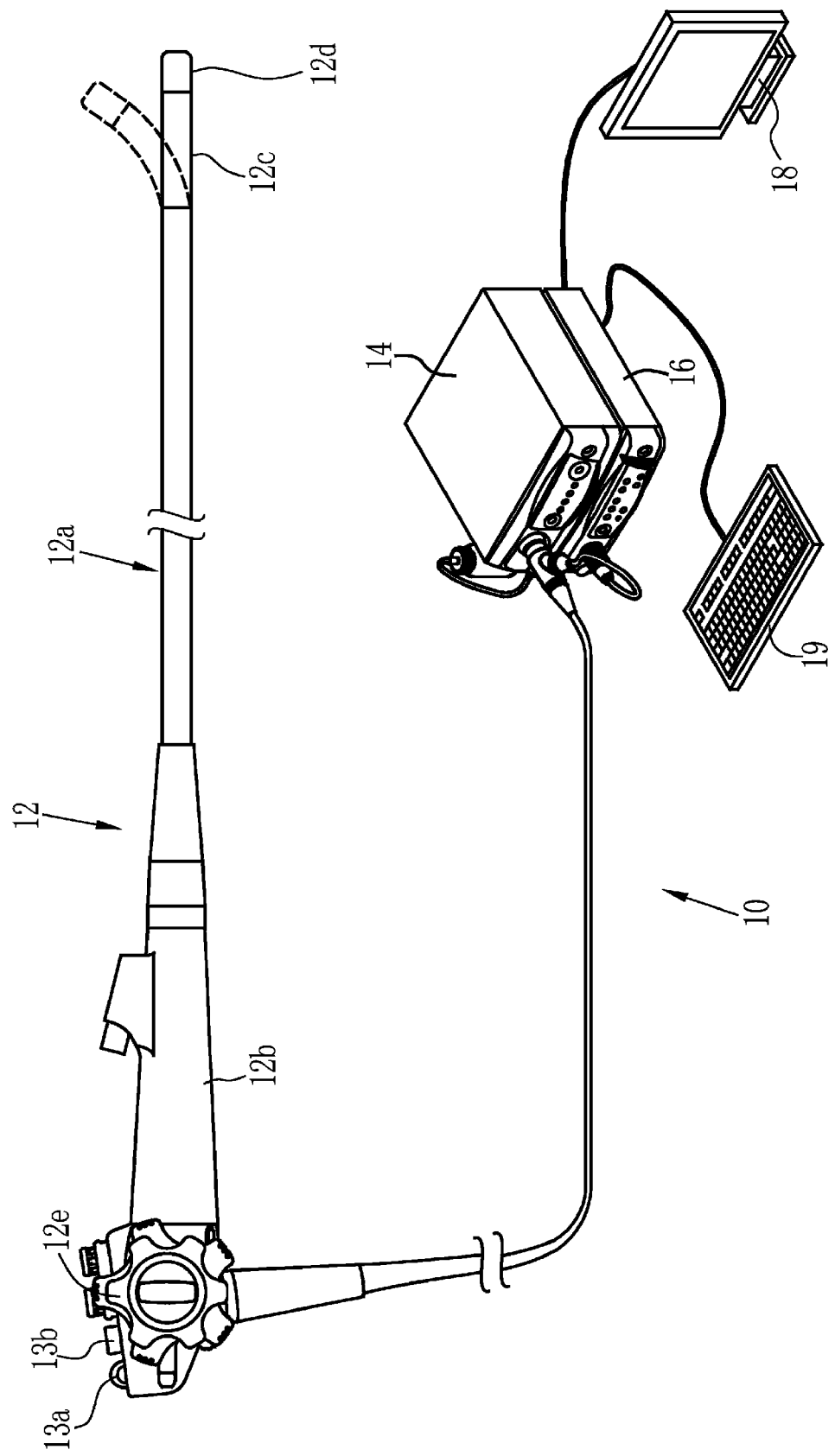
FIG. 1 is an external view of an endoscope system.

As illustrated in FIG. 1, an endoscope system 10 (endoscope apparatus) includes an endoscope 12, a light source device 14, a processor device 16, a monitor 18, and a console 19. The endoscope 12 captures an image of a photographic subject. The light source device 14 generates illumination light. The processor device 16 performs, for example, system control and image processing of the endoscope system 10. The monitor 18 is a display unit that displays, for example, an image captured by the endoscope 12. The console 19 is an input device for, for example, inputting settings to, for example, the processor device 16.

The endoscope 12 has an insertion part 12a that is inserted into a subject, an operation part 12b that is provided on the proximal end part of the insertion part 12a, a bending part 12c that is provided on the distal end side of the insertion part 12a, and a tip part 12d. When an angle knob 12e of the operation part 12b is operated, the bending part 12c bends. As a result, the tip part 12d turns in a desired direction. In addition to the angle knob 12e, the operation part 12b is provided with a zoom operation part 13a and a mode switching operation part 13b. When the zoom operation part 13a is operated, an enlarged or reduced image of a photographic subject is captured. When the mode switching operation part 13b is operated, an operation mode switches. The operation mode is the operation form of one of the endoscope 12, the light source device 14, or the processor device 16, or a combination of the operation forms of two or more of these.

Specifically, the operation mode is determined on the basis of the type of illumination light that is used in image capturing of a photographic subject, whether or not an optical enlargement process is performed, or whether or not image processing is performed (including a combination of these). For convenience sake, the same applies to a case where the operation mode of the endoscope 12, the operation mode of the light source device 14, or the operation mode of the processor device 16 is mentioned. The type of illumination light means the type of illumination light that can be identified with the wavelength, wavelength range, or spectrum of the illumination light. The optical enlargement process means an enlargement process using a zoom lens 47 (see FIG. 2), that is, optical zooming. Whether or not the optical enlargement process is performed means whether optical enlargement is performed or optical enlargement is not performed. Whether or not the optical enlargement process is performed includes a case where it is assumed that the optical enlargement process is performed if the optical enlargement process is performed with a specific enlargement ratio or more and where, on the contrary, it is not assumed that the optical enlargement process is performed even though optical zooming is performed if the optical enlargement process is performed with less than the specific enlargement ratio (that is, a case where the magnitude of the enlargement ratio in the optical enlargement process is taken into consideration). Note that the endoscope system 10 can perform an electronic enlargement process instead of the optical enlargement process or in combination with the optical enlargement process. The electronic enlargement process is a process for enlarging part of an endoscopic image, that is, electronic zooming. The image processing based on which the operation mode is determined means some or all of the various processes performed by an image processing unit 61 (see FIG. 2) for an endoscopic image. Whether or not the image processing is performed means whether specific image processing is performed or specific image processing is not performed. Whether or not the image processing is performed includes a case where it is assumed that the image processing is performed if the image processing is performed with a specific intensity or more and where it is not assumed that the image processing is performed if the image processing is performed with less than the specific intensity (that is, a case where the magnitude of the intensity of the image processing is taken into consideration).

The endoscope system 10 has, for example, a normal observation mode in which image capturing of a photographic subject is performed with white light to display the photographic subject in a natural color tone and a special observation mode in which image capturing of a photographic subject is performed with illumination light having a specific wavelength range different from that of white light to display the photographic subject. The special observation mode includes, for example, a mode in which image capturing of a photographic subject is performed by using illumination light that contains a larger amount of blue or violet components than white light that is used in the normal observation mode to facilitate observation of specific tissue or structure, such as a very thin blood vessel, and a mode in which the color of an endoscopic image is modulated to facilitate observation of a specific lesion or the like. Hereinafter, the plurality of classified special observation modes are simply referred to as the special observation mode unless otherwise required, and only the normal observation mode and the special observation mode are distinguished from each other.

Figure 2:
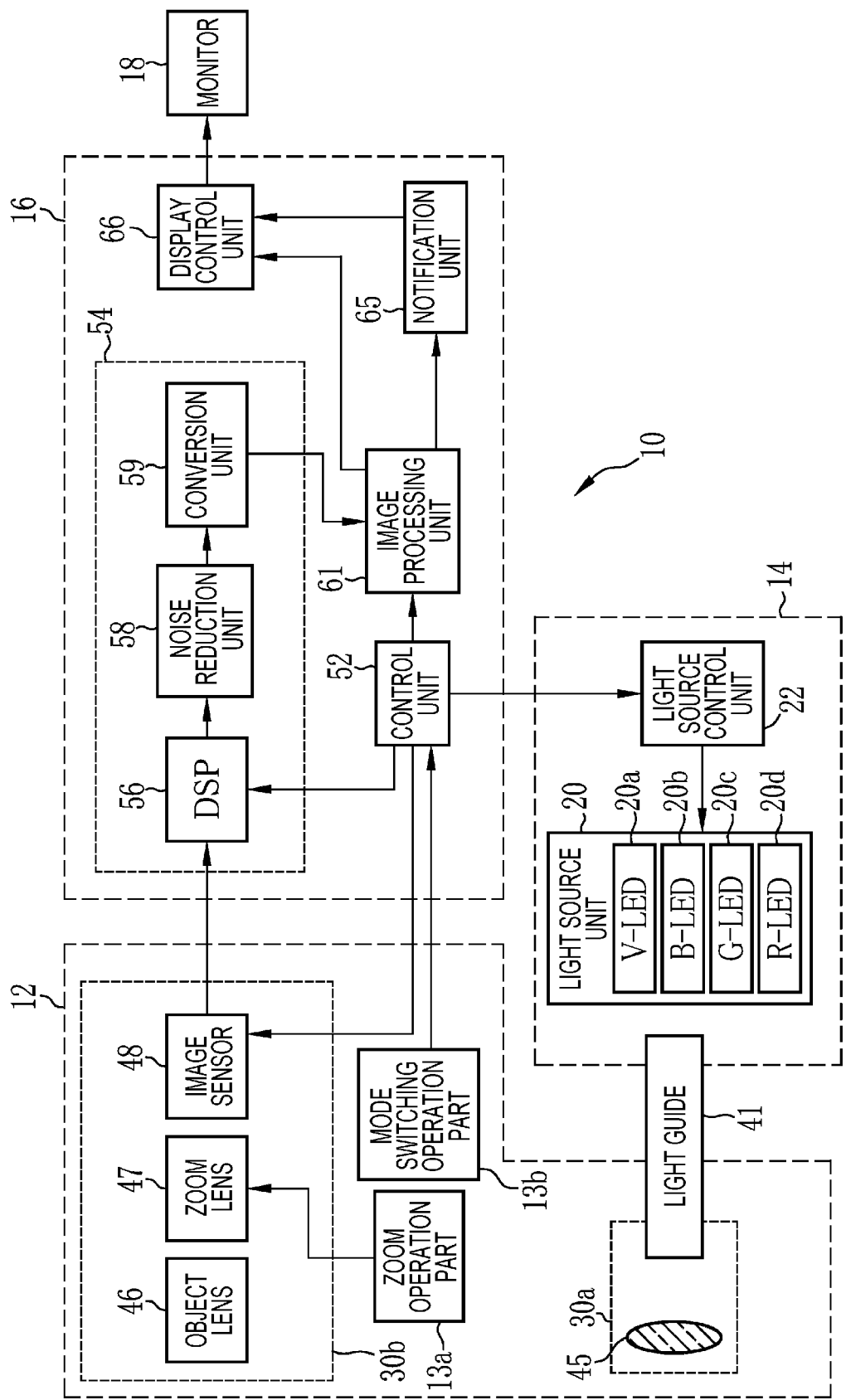
FIG. 2 is a block diagram of the endoscope system.

As illustrated in FIG. 2, the light source device 14 includes a light source unit 20 that emits illumination light and a light source control unit 22 that controls operations of the light source unit 20.

The light source unit 20 emits illumination light that illuminates a photographic subject. Emission of illumination light includes emission of, for example, excitation light that is used to emit illumination light. The light source unit 20 includes a light source formed of, for example, a laser diode (hereinafter referred to as an LD), an LED (light emitting diode), a xenon lamp, or a halogen lamp and emits at least illumination light in a white color or excitation light that is used to emit illumination light in the white color. The white color includes a pseudo white color that is substantially equivalent to a white color in image capturing of a photographic subject using the endoscope 12. The light source unit 20 includes, for example, a fluorescent body that emits light when irradiated with excitation light or an optical filter for adjusting, for example, the wavelength range, spectrum, or amount of light of the illumination light or excitation light as necessary. In addition, the light source unit 20 can emit light having a specific wavelength range necessary for capturing an image that is used to calculate biological information, such as the oxygen saturation of hemoglobin contained in the photographic subject.

In this embodiment, the light source unit 20 has LEDs in four colors, namely, a V-LED 20a, a B-LED 20b, a G-LED 20c, and an R-LED 20d. The V-LED 20a emits violet light VL having a center wavelength of 405 nm and a wavelength range of 380 to 420 nm. The B-LED 20b emits blue light BL having a center wavelength of 460 nm and a wavelength range of 420 to 500 nm. The G-LED 20c emits green light GL having a wavelength range of 480 to 600 nm. The R-LED 20d emits red light RL having a center wavelength of 620 to 630 nm and a wavelength range of 600 to 650 nm. The center wavelengths of the V-LED 20a and the B-LED 20b have a width of about ±20 nm, and preferably, about +5 nm to about 10 nm.

The light source control unit 22 controls, for example, the timing at which each light source that constitutes the light source unit 20 is turned on, turned off, or blocked and the amount of light emission of each light source. As a result, the light source unit 20 can emit a plurality of types of illumination light having different spectra. In this embodiment, the light source control unit 22 controls, for example, turning-on and turning-off of each of the LEDs 20a to 20d, the amounts of light emission during turning-on, and insertion and removal of the optical filter by inputting independent control signals to the LEDs 20a to 20d to thereby adjust the spectrum of illumination light. Accordingly, the light source unit 20 emits white light in the normal observation mode. The light source unit 20 can at least emit illumination light formed of violet light in a narrow band. The "narrow band" means a substantially single wavelength range in relation to the characteristics of the photographic subject and/or the spectral characteristics of color filters of an image sensor 48. For example, in a case where light has a wavelength range of, for example, about ±20 nm or less (preferably, about ±10 nm or less) with reference to the center wavelength, the light is in a narrow band.

In the tip part 12d of the endoscope 12, an illumination optical system 30a and an imaging optical system 30b are provided. Illumination light from the light source unit 20 is propagated to the illumination optical system 30a through a light guide 41. The illumination optical system 30a has an illumination lens 45, and illumination light is emitted toward a photographic subject via the illumination lens 45.

The imaging optical system 30b has an object lens 46, the zoom lens 47, and the image sensor 48. The image sensor 48 captures an image of a photographic subject by using, for example, reflected light (in addition to the reflected light, scattered light, fluorescent light emitted from the photographic subject, or fluorescent light caused by a drug administered to the photographic subject is included) resulting from illumination light and returning from the photographic subject via the object lens 46 and the zoom lens 47. The zoom lens 47 moves in response to an operation of the zoom operation part 13a to enlarge or reduce an image of the photographic subject.

The image sensor 48 has, for each pixel, a color filter in one color among color filters in a plurality of colors. In this embodiment, the image sensor 48 is a color sensor having color filters in primary colors. Specifically, the image sensor 48 has R pixels each having a red filter (R filter), G pixels each having a green filter (G filter), and B pixels each having a blue filter (B filter).

Note that as the image sensor 48, a CCD (charge-coupled device) sensor or a CMOS (complementary metal-oxide semiconductor) sensor can be used. Although the image sensor 48 of this embodiment is a primary color sensor, a complementary color sensor can also be used. A complementary color sensor has, for example, cyan pixels each of which is provided with a cyan filter, magenta pixels each of which is provided with a magenta filter, yellow pixels each of which is provided with a yellow filter, and green pixels each of which is provided with a green filter. In a case where a complementary color sensor is used, an image obtained from the above-described pixels in the respective colors can be converted to an image similar to an image obtained by using a primary color sensor by performing conversion from complementary colors to primary colors. The same applies to a primary color sensor or a complementary color sensor having one or more types of pixels, such as W pixels (white pixels that receive light in substantially all wavelength ranges), having characteristics other than the above. Although the image sensor 48 of this embodiment is a color sensor, a monochrome sensor having no color filters may be used.

The processor device 16 has a control unit 52, an image obtaining unit 54, the image processing unit 61, a notification unit 65, and a display control unit 66 (see FIG. 2).

The control unit 52 centrally controls the endoscope system 10 and controls, for example, synchronization between the timing of irradiation with illumination light and the timing of image capturing. In a case where, for example, various settings are input by using, for example, the console 19, the control unit 52 inputs the settings to the respective units of the endoscope system 10, such as the light source control unit 22, the image sensor 48, and the image processing unit 61.

The image obtaining unit 54 obtains from the image sensor 48 an image obtained by image capturing of a photographic subject using the pixels in the respective colors, that is, a raw image. The raw image is an image that is not yet subjected to demosaicing. An image obtained from the image sensor 48 and subjected to a process, such as a noise reducing process, is also a raw image as long as the image is not yet subjected to demosaicing.

The image obtaining unit 54 includes a DSP (digital signal processor) 56, a noise reduction unit 58, and a conversion unit 59 that perform various processes for the obtained raw image as necessary to generate an endoscopic image.

The DSP 56 includes, for example, an offset processing unit, a defect correction processing unit, a demosaicing processing unit, a interpolation processing unit, a linear matrix processing unit, and a YC conversion processing unit (none of which are illustrated). The DSP 56 uses these units to perform various processes for a raw image or an image generated by using a raw image.

The offset processing unit performs an offset process for a raw image. The offset process is a process for reducing dark current components in a raw image to set an accurate zero level. The offset process may be called a clamping process. The defect correction processing unit performs a defect correction process for a raw image. The defect correction process is a process for, in a case where the image sensor 48 includes a pixel (defective pixel) having a defect caused by a manufacturing process or by aging, correcting or generating the pixel value of a raw pixel corresponding to the defective pixel of the image sensor 48. The demosaicing processing unit performs a demosaicing process for raw images in the respective colors corresponding to the respective color filters. The demosaicing process is a process for generating a pixel value, of a raw image, that is missing due to the arrangement of the color filters, by interpolation. The linear matrix processing unit performs a linear matrix process for an endoscopic image generated by allocating one or more raw images to R, G, and B channels. The linear matrix process is a process for increasing the color reproducibility of the endoscopic image. The YC conversion processing unit performs a process for converting the endoscopic image generated by allocating one or more raw images to the R, G, and B channels to an endoscopic image having a luminance channel Y, a color difference channel Cb, and a color difference channel Cr.

The noise reduction unit 58 performs a noise reduction process for the endoscopic image having the luminance channel Y, the color difference channel Cb, and the color difference channel Cr by using, for example, a moving average method or a median filtering method. The conversion unit 59 reconverts the endoscopic image having the luminance channel Y, the color difference channel Cb, and the color difference channel Cr and subjected to the noise reduction process to an endoscopic image having the channels of the respective colors of R, G, and B.

Figure 3:
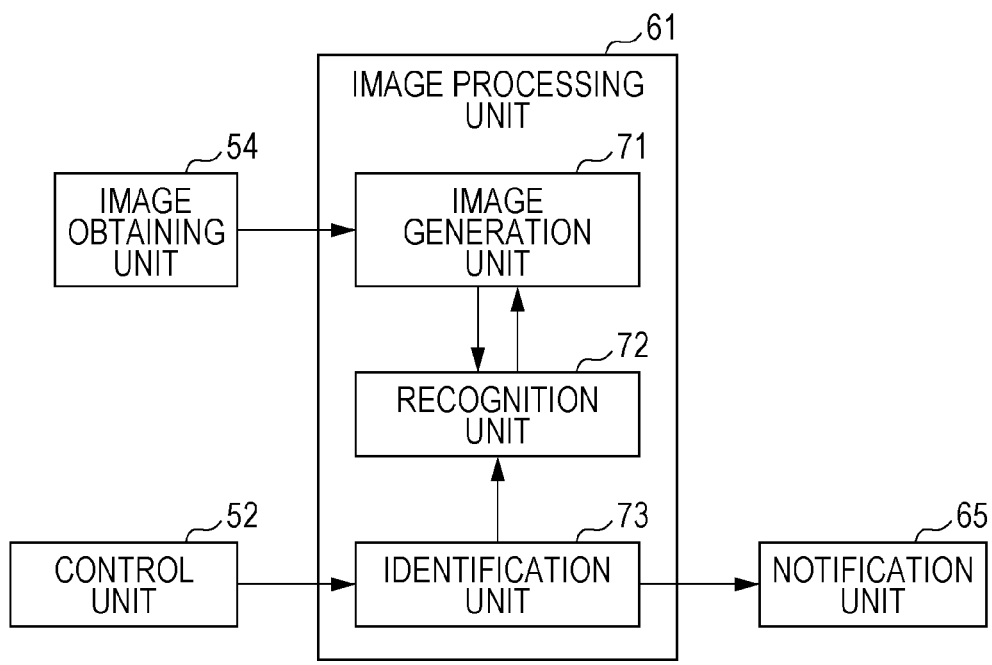
FIG. 3 is a block diagram of an image processing unit.

The image processing unit 61 performs for an endoscopic image output by the image obtaining unit 54, necessary image processing in accordance with, for example, the observation mode. The image processing unit 61 uses the endoscopic image to perform a recognition process of recognizing a photographic subject having specific characteristics or part of the photographic subject. Specifically, as illustrated in FIG. 3, the image processing unit 61 includes, for example, an image generation unit 71, a recognition unit 72, and an identification unit 73.

The image generation unit 71 obtains an endoscopic image from the image obtaining unit 54 and generates an endoscopic image that is used in, for example, display on the monitor 18. For example, the image generation unit 71 obtains from the image obtaining unit 54 a B image obtained by image capturing of a photographic subject using the B pixels, a G image obtained by image capturing of the photographic subject using the G pixels, and an R image obtained by image capturing of the photographic subject using the R pixels and uses all or some of the images to generate an endoscopic image for display.

When generating an endoscopic image for display, the image generation unit 71 performs for an endoscopic image obtained from the image obtaining unit 54 or for an image generated by using an endoscopic image obtained from the image obtaining unit 54, necessary image processing in accordance with, for example, the observation mode. The image processing performed by the image generation unit 71 is, for example, a highlighting process of highlighting a photographic subject or part of the photographic subject. Highlighting means to distinguish a specific part from, for example, the other tissue or structures to allow obtaining of information about the specific part. For example, a process for outlining a part having specific characteristics with a frame to display the outline or a process for, for example, changing the color or brightness of the part having specific characteristics relative to the other parts (for example, a normal mucous membrane) is the highlighting process. "Allowing obtaining of information about the specific part" includes allowing recognition of, for example, the position, shape, color or brightness, and/or size (area) of the specific part and also includes allowing knowing or obtaining of biological function information (for example, the oxygen saturation or the blood vessel concentration) about the specific part.

The recognition unit 72 performs the recognition process of recognizing a photographic subject by using an image obtained by image capturing of the photographic subject. "Recognizing a photographic subject" means to detect the presence or absence of a part of a photographic subject having specific characteristics (including a case of detecting the entire photographic subject), determine the type or the degree of progression of a part of a photographic subject having specific characteristics (including determination of the entire photographic subject), and/or obtain (for example, calculate) biological function information about a photographic subject in part or in whole. A part of a photographic subject having specific characteristics is, for example, a lesion or a potential lesion (hereinafter referred to as a lesion or the like). That is, the recognition unit 72 can recognize the presence or absence of a lesion or the like by the recognition process. Further, the recognition unit 72 can recognize the type or the degree of progression of a lesion or the like by the recognition process. Recognition of the type of a lesion or the like means, in a case where the lesion or the like is a polyp, to determine the type, such as adenoma, hypertrophic polyp, or cancer. Recognition of the degree of progression of a lesion or the like means, in a case where the lesion or the like is cancer, to determine the stage of the cancer or determine, for example, the NICE (NBI (Narrow-Band Imaging) International Colorectal Endoscopic) classification or the JNET (The Japan NBI Expert Team) classification. In this embodiment, an image obtained by image capturing of a photographic subject is an endoscopic image obtained from the image obtaining unit 54 or an endoscopic image generated by the image generation unit 71. Further, in this embodiment, the recognition unit 72 detects a lesion or the like by the recognition process.

The recognition unit 72 is, for example, an artificial intelligence (AI) having a learning function. Specifically, the recognition unit 72 is an AI trained by using a machine learning algorithm, such as a neural network (NN), a convolutional neural network (CNN), AdaBoost, or a random forest. Further, the recognition unit 72 is trained using specific images in order to perform the recognition process, and therefore, even if the recognition unit 72 can perform the recognition process using the other images, the accuracy of the result of the recognition process may be low. In this embodiment, the recognition unit 72 is an AI trained in order to detect a lesion or the like using an endoscopic image for display obtained in the normal observation mode. "Having a learning function" means to have an ability to learn and includes a trained state. Note that the recognition unit 72 might not be configured as an AI and can be configured to calculate a feature value from an image and to, for example, perform detection by using the calculated feature value.

The recognition unit 72 inputs the result of the recognition process to the image generation unit 71 or to the display control unit 66 in accordance with the details of the recognition process. When the recognition unit 72 inputs the result of the recognition process to the image generation unit 71, the image generation unit 71 generates an endoscopic image for display that reflects the result of the recognition process. When the recognition unit 72 inputs the result of the recognition process to the display control unit 66, the display control unit 66 displays the result of the recognition process on the screen of the monitor 18 together with the endoscopic image obtained from the image generation unit 71. The recognition unit 72 inputs the result of the recognition process to the image generation unit 71 in a case where, for example, the color of the endoscopic image for display is changed in accordance with a value of biological function information, which is the result of the recognition process. The recognition unit 72 inputs the result of the recognition process to the display control unit 66 in a case where, for example, the position of a lesion or the like, which is the result of the recognition process, is to be indicated by, for example, displaying a frame that is superimposed on the endoscopic image. In this embodiment, the recognition unit 72 inputs information about, for example, the position of a detected lesion or the like, which is the result of the recognition process, to the image generation unit 71. The image generation unit 71 generates an endoscopic image for display for which the highlighting process is performed for a part in which the lesion or the like is present.

The identification unit 73 identifies the type of an image obtained by image capturing of a photographic subject. "Identifying the type of image" means to determine whether the recognition process to be performed by the recognition unit 72 functions for a certain type of image. That is, the identification unit 73 identifies the type of image as one of the two types, namely, an image for which the recognition process functions and an image for which the recognition process does not function. An image for which the recognition process functions is an image for which, when the recognition process is performed, a result having an accuracy higher than or equal to a specific accuracy is expected. An image for which the recognition process does not function is an image for which, when the recognition process is performed, only a result having an accuracy lower than the specific accuracy is expected. For example, in a case where the recognition unit 72 is an AI, an image of a type the same as the type of images used to train the recognition unit 72 is an image for which the recognition process functions, and images of the other types are images for which the recognition process does not function. The specific accuracy is a reference value of, for example, the correctness or reliability of the recognition process sufficient for supporting, for example, diagnoses. In this embodiment, in the recognition unit 72, an endoscopic image obtained in the normal observation mode is an image for which the recognition process functions, and an endoscopic image obtained in the special observation mode is an image for which the recognition process does not function.

Specifically, the identification unit 73 identifies the type of image by determining the operation mode, the model of the endoscope 12 used in image capturing of the photographic subject, or whether or not a drug is administered to the photographic subject.

The identification unit 73 can determine the operation mode with reference to setting information (including an electric signal generated in response to switching of the operation mode) about the operation mode obtained from the control unit 52. For example, in a case where the operation mode is the normal observation mode, the identification unit 73 identifies an image obtained by image capturing of a photographic subject as an image for which the recognition process functions. The identification unit 73 can determine the operation mode by analyzing an endoscopic image obtained from the image obtaining unit 54 or an endoscopic image generated by the image generation unit 71. For example, the identification unit 73 can analyze, for example, the color or the distribution of brightness (unevenness of illumination light) of the endoscopic image or the size of the photographic subject (for example, the presence or absence of a pit pattern or the average thickness thereof) and use the result to determine the operation mode.

The identification unit 73 can determine the model of the endoscope 12 with reference to information about the model of the endoscope 12 obtained from the control unit 52. When the identification unit 73 determines the model of the endoscope 12, the identification unit 73 determines the type of the image sensor 48 (for example, the characteristics of the color filters) mounted in the endoscope 12 accordingly. Therefore, the identification unit 73 can determine whether the recognition process functions for an image captured by using the endoscope 12 of the determined model. The information about the model of the endoscope 12 is obtained by the control unit 52 from the endoscope 12 when the endoscope 12 is connected to the light source device 14 or to the processor device 16.

The identification unit 73 can determine whether or not a drug is administered to the photographic subject by obtaining setting information about drug administration obtained from the control unit 52. Further, the identification unit 73 can determine whether or not a drug is administered to the photographic subject by analyzing an endoscopic image obtained from the image obtaining unit 54 or an endoscopic image generated by the image generation unit 71. Administration of a drug to a photographic subject includes spraying of a coloring agent, such as indigo carmine, on the surface of the photographic subject and also includes intravenous injection of a fluorescent drug, such as indocyanine green (ICG), into the photographic subject.

In this embodiment, the identification unit 73 determines whether the operation mode is the normal observation mode or the special observation mode to thereby identify the type of image. The identification unit 73 uses setting information about the operation mode obtained from the control unit 52 when determining the operation mode.

The identification unit 73 identifies the type of image as described above and activates the recognition unit 72 in a case where the identified image is an image of a type for which the recognition process functions and where the recognition unit 72 is inactive (a state where the recognition unit 72 does not perform the recognition process). On the other hand, in a case where the identified image is an image of a type for which the recognition process does not function and where the recognition unit 72 is active (a state where the recognition unit 72 performs the recognition process), the identification unit 73 inactivates the recognition unit 72. Accordingly, the recognition unit 72 is automatically activated in a case where the type of image is a type for which the recognition process functions, and is automatically inactivated in a case where the type of image is a type for which the recognition process does not function.

The notification unit 65 obtains from the identification unit 73 information about whether the recognition process functions. The notification unit 65 gives a notification of whether the recognition process functions for an image of a specific type identified by the identification unit 73. "Giving a notification" of whether the recognition process functions means to allow a doctor or the like, who is a user, to know the status, that is, whether the recognition process functions. For example, the notification unit 65 can give a notification of whether the recognition process functions by displaying or not displaying on the screen of the monitor 18, for example, a message (character string), a letter, a geometric shape, and/or a symbol (including display of, for example, a mark, an icon, or an indicator) or by changing the display. In addition, the notification unit 65 can give a notification of whether the recognition process functions by, for example, lighting, extinguishing, or blinking a lamp, a sound (including voice), or vibrating a member having a vibration function, or by changing these. As a matter of course, the notification unit 65 can give a notification of whether the recognition process functions by combining, for example, a character string and lighting of a lamp. In this embodiment, the notification unit 65 performs display on the screen of the monitor 18 indicating whether the recognition process functions.

The notification unit 65 gives a notification of whether the recognition process functions at least in a case where the type of image switches. The case where the type of image switches is a case where the result of identification by the identification unit 73 changes. In this embodiment, the notification unit 65 continuously gives a notification of whether the recognition process functions including the case where the type of image switches. However, the notification unit 65 can give a notification of whether the recognition process functions for a predetermined period in the case where the type of image switches and can stop giving a notification of whether the recognition process functions during a period other than the predetermined period, in accordance with a setting. This setting is effective in a case where the doctor or the like feels annoying about such a continuous notification.

The display control unit 66 converts an endoscopic image output by the image processing unit 61 to an endoscopic image in a form suitable for display and outputs the endoscopic image to the monitor 18. Then, the monitor 18 displays the endoscopic image. In this embodiment, the notification unit 65 inputs information indicating whether the recognition process functions to the display control unit 66. Then, the display control unit 66 displays the information on the screen of the monitor 18.

Figure 4:
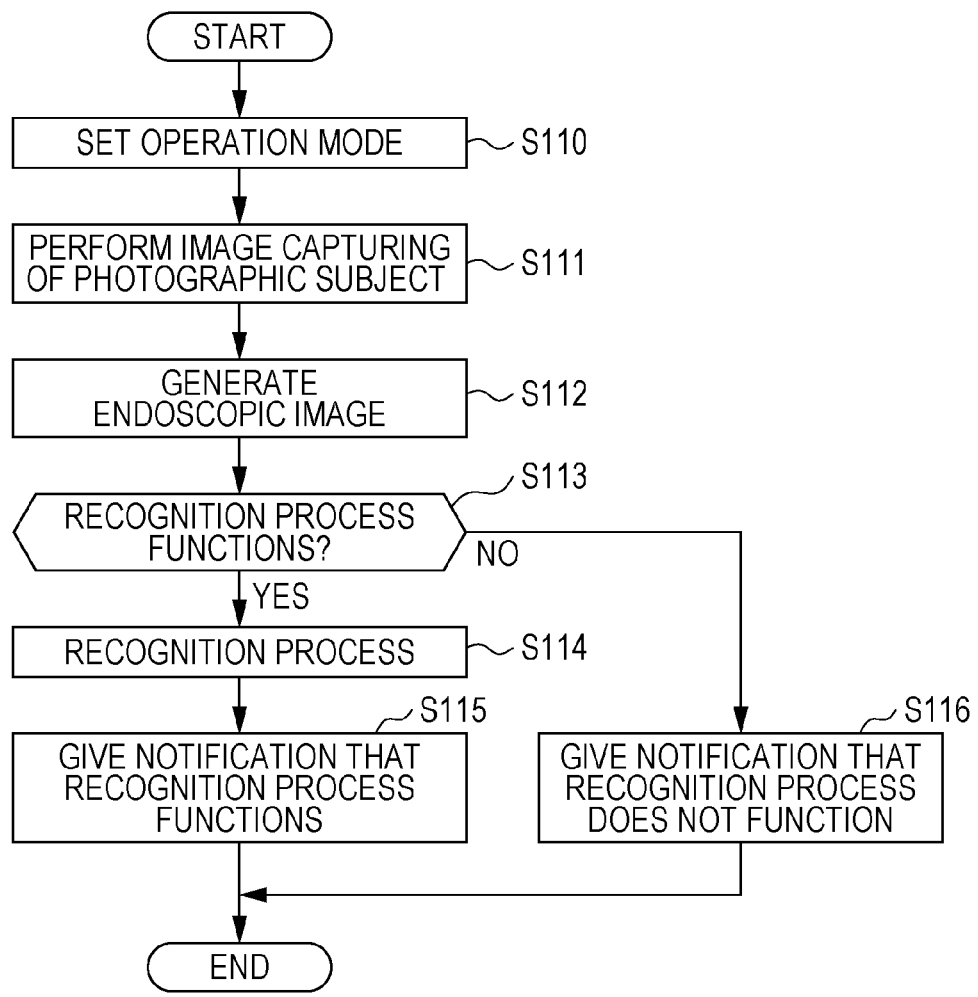
FIG. 4 is a flowchart of a first embodiment.

The endoscope system 10 configured as described above operates as follows to give a notification of whether the recognition process functions. As illustrated in FIG. 4, when a doctor or the like operates the mode switching operation part 13b to set the operation mode (step S110) and performs image capturing of a photographic subject (step S111), the image obtaining unit 54 obtains an endoscopic image. The image generation unit 71 performs necessary image processing and generates an endoscopic image for display (step S112). Meanwhile, the identification unit 73 determines whether the recognition process functions for the image (step S113 (determination function)). In a case where the recognition process functions (YES in step S113), the recognition unit 72 performs the recognition process (step S114), and the notification unit 65 gives a notification that the recognition process functions (step S115). In a case where the recognition process does not function (NO in step S113), the recognition unit 72 does not perform the recognition process, and the notification unit 65 gives a notification that the recognition process does not function (step S116).

Figure 5:
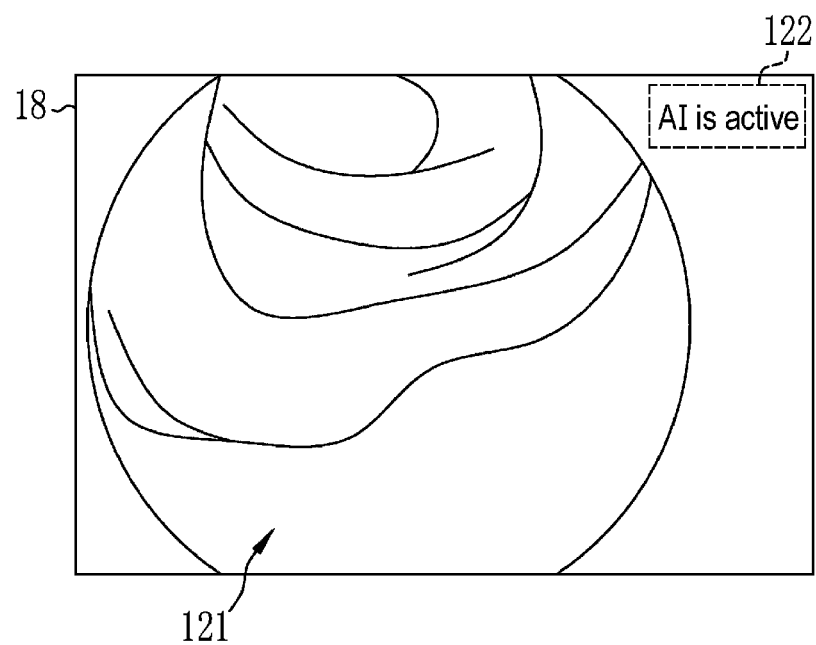
FIG. 5 illustrates an example of display giving a notification that a recognition process functions.

More specifically, in a case where the operation mode is the normal observation mode, the image generation unit 71 generates a normal observation image 121 that is an endoscopic image representing the photographic subject in a natural color tone. Then, as illustrated in FIG. 5, the display control unit 66 displays the normal observation image 121 on the screen of the monitor 18. Further, the identification unit 73 of this embodiment identifies the normal observation image 121 as an image for which the recognition process functions, and therefore, the recognition unit 72 performs the recognition process. Then, the notification unit 65 gives a notification that the recognition process functions by, for example, display 122 "AI is active". As a result, a doctor or the like can correctly recognize the result of the recognition process. Specifically, a lesion or the like that is the result of the recognition process is not present in the normal observation image 121. Therefore, without a notification by the display 122 "AI is active", the doctor or the like is unable to recognize whether a lesion or the like is not present as a result of performing the recognition process or a lesion or the like is not present as a result of not performing the recognition process. However, with the notification by the display 122 "AI is active", the doctor or the like can correctly recognize that a lesion or the like is not present in the normal observation image 121 as a result of the recognition unit 72 performing the recognition process.

Figure 6:
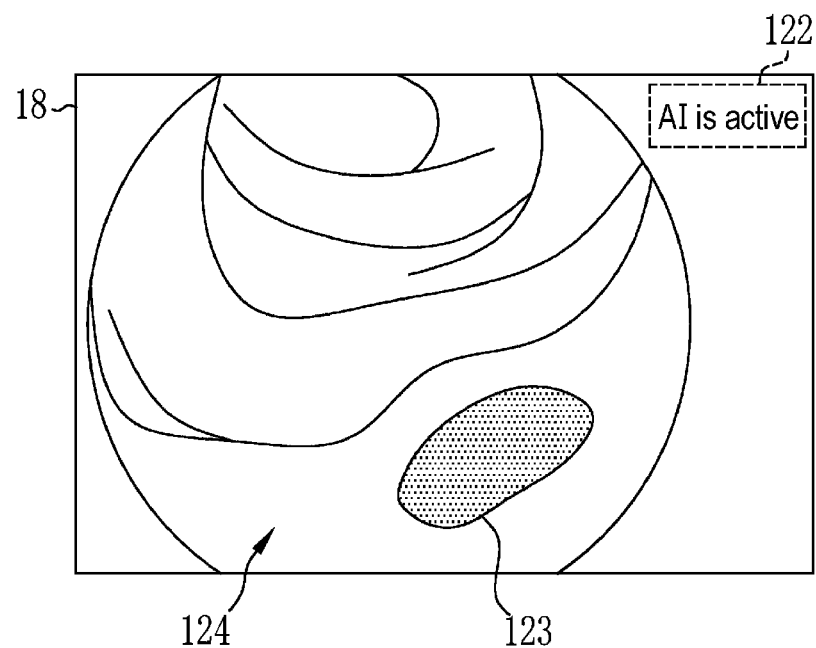
FIG. 6 illustrates an example of display giving a notification that a recognition process functions.

As illustrated in FIG. 6, in a case where an image of a photographic subject having a lesion or the like 123 is captured in the normal observation mode, the image generation unit 71 generates a normal observation image 124 in which the lesion or the like 123 is highlighted as a result of the recognition process, and the display control unit 66 displays the normal observation image 124 on the monitor 18. In this case, without a notification by the display 122 "AI is active", the doctor or the like may have difficulty in recognizing whether the lesion or the like 123 in the normal observation image 124 is highlighted as a result of the recognition process or the lesion or the like 123 is the original lesion or the like for which, for example, the highlighting process is not performed. With the notification by the display 122 "AI is active", the doctor or the like can correctly recognize that the lesion or the like 123 is highlighted as a result of the recognition unit 72 performing the recognition process.

Figure 7:
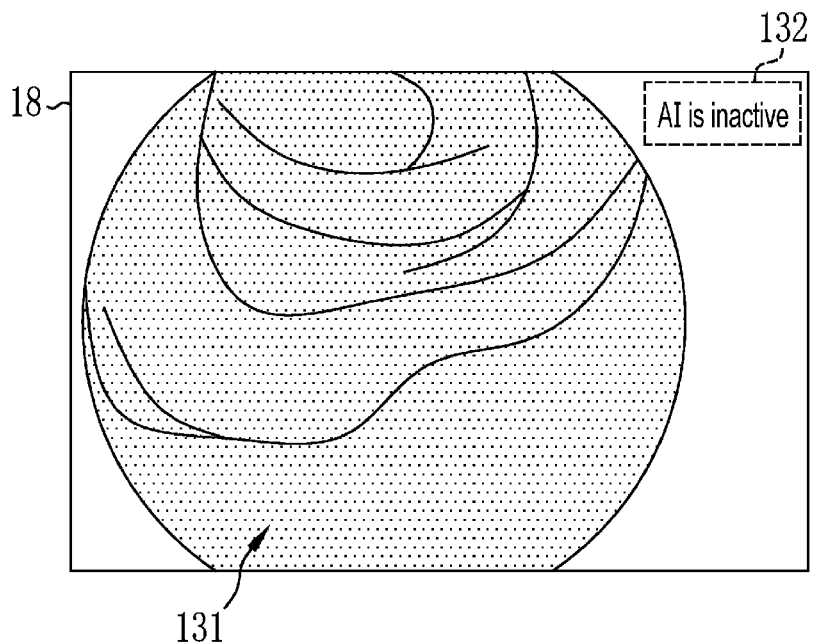
FIG. 7 illustrates an example of display giving a notification that a recognition process does not function.

Meanwhile, as illustrated in FIG. 7, in a case where a photographic subject is observed in the special observation mode, the image generation unit 71 generates, for example, a special observation image 131 in a form different from the form of the normal observation image 121, and the display control unit 66 displays the special observation image 131 on the screen of the monitor 18. In this case, the identification unit 73 of this embodiment identifies the special observation image 131 as an image for which the recognition process does not function, and therefore, the recognition unit 72 does not perform the recognition process. Then, the notification unit 65 gives a notification that the recognition process does not function by, for example, display 132 "AI is inactive". As a result, the doctor or the like can correctly recognize the result of the recognition process. Specifically, a lesion or the like that is the result of the recognition process is not present in the special observation image 131. Therefore, without the notification by the display 132 "AI is inactive", the doctor or the like is unable to recognize whether a lesion or the like is not present as a result of performing the recognition process or a lesion or the like is not present as a result of not performing the recognition process. Specifically, in a case where the doctor or the like has a preconception that the endoscope system 10 performs the recognition process, even when the recognition unit 72 does not perform the recognition process, the doctor or the like may incorrectly recognize the displayed result that no lesion or the like is present in the special observation image 131 as a result of performing the recognition process, and the accuracy of diagnosis may decrease. However, with the notification by the display 132 "AI is inactive", the doctor or the like can recognize that the recognition process is not performed, and therefore, the doctor or the like observes the special observation image 131 without incorrect recognition as described above and can make a correct diagnosis.

As described above, with the endoscope system 10, it is possible to prevent incorrect recognition of the result of performing the recognition process and the result of not performing the recognition process. As a consequence, it is possible to prevent wrong diagnoses.

Figure 8:
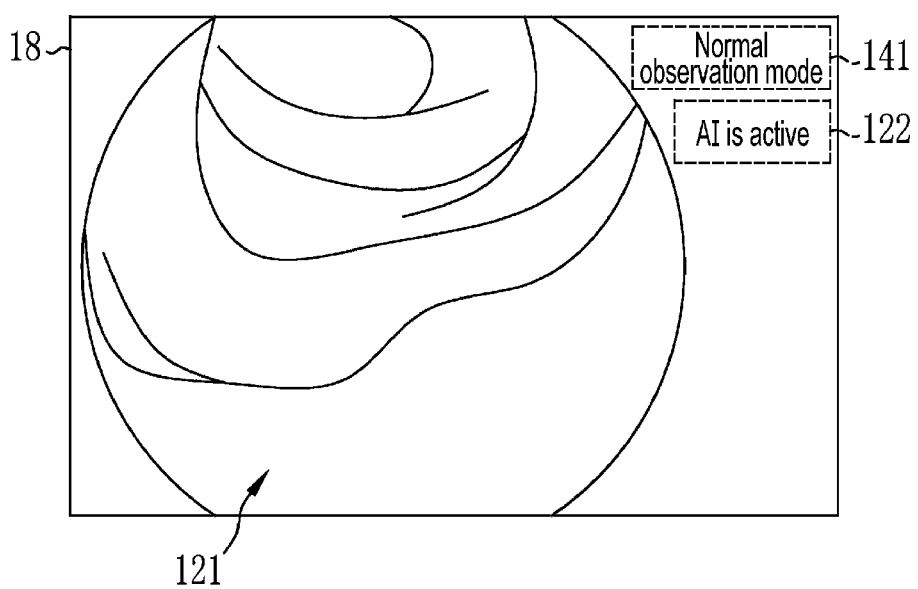
FIG. 8 illustrates an example of display displaying an operation mode.

Note that in the first embodiment described above, the notification unit 65 displays on the screen of the monitor 18 the display 122 "AI is active" or the display 132 "AI is inactive" to thereby give a notification of whether the recognition process functions; however, the notification unit 65 can also provide information other than the notification of whether the recognition process functions. For example, the notification unit 65 can provide information, in part or in whole, used by the identification unit 73 to identify the type of image. In the first embodiment, the identification unit 73 identifies the type of image with reference to setting information about the operation mode, and therefore, as illustrated in FIG. 8, the notification unit 65 can give a notification of the operation mode by, for example, display 141 "normal observation mode" on the screen of the monitor 18. The same applies to a case where the identification unit 73 identifies the type of image with reference to information other than the information about the operation mode.

Figure 9:
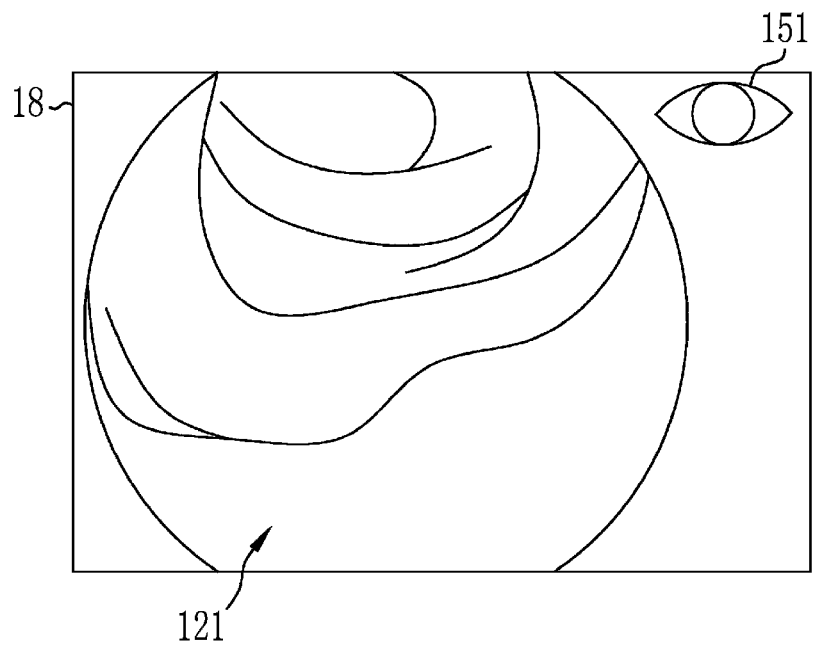
FIG. 9 illustrates an example of display giving a notification that a recognition process functions by displaying an icon.
Figure 10:
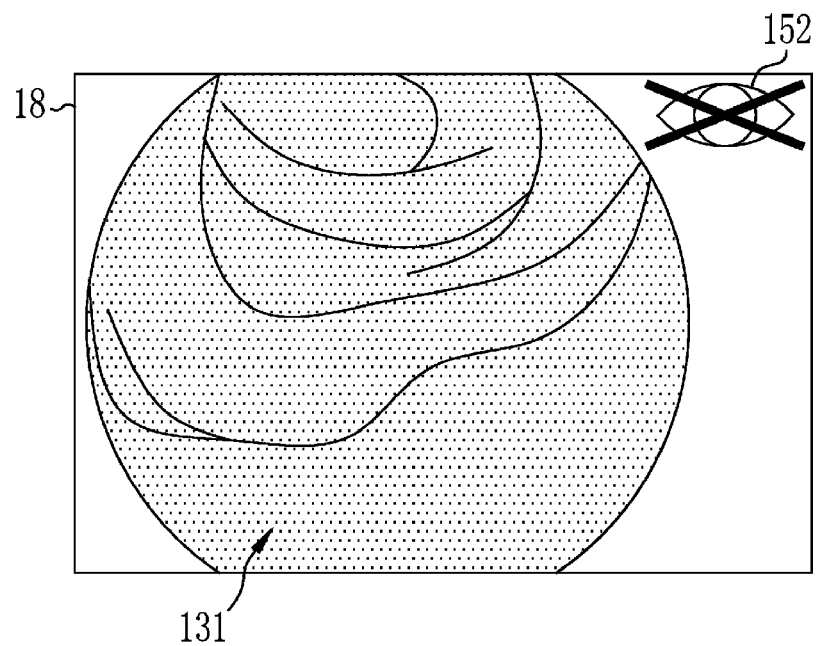
FIG. 10 illustrates an example of display giving a notification that a recognition process does not function by displaying an icon.
Figure 11:
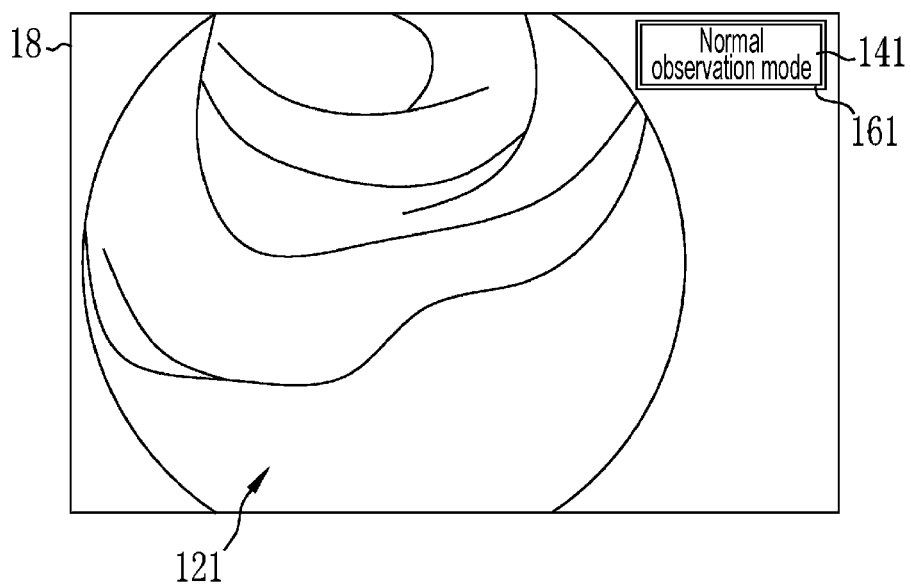
FIG. 11 illustrates another example of display giving a notification that a recognition process functions.
Figure 12:
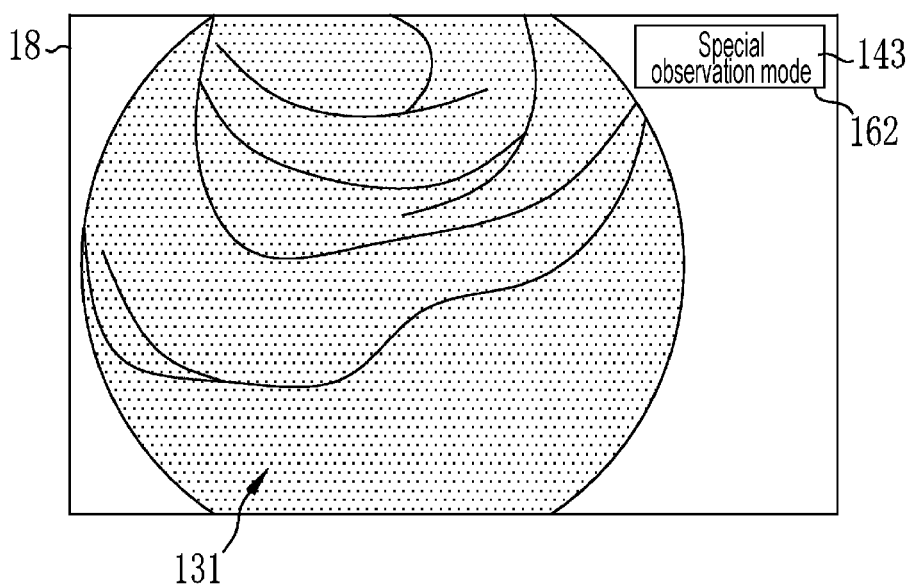
FIG. 12 illustrates another example of display giving a notification that a recognition process does not function.

Further, in the first embodiment described above, the notification unit 65 displays on the screen of the monitor 18 the display 122 "AI is active" or the display 132 "AI is inactive" to thereby give a notification of whether the recognition process functions; however, the notification of whether the recognition process functions may be given in any form. For example, as illustrated in FIG. 9, the notification unit 65 can display an icon 151 indicating that "AI is active" instead of the display 122 using the character string "AI is active" to give a notification that the recognition process is functioning. Similarly, as illustrated in FIG. 10, the notification unit 65 can display an icon 152 indicating that "AI is inactive" instead of the display 132 using the character string "AI is inactive" to give a notification that the recognition process is not functioning. In a case where the notification of whether the recognition process functions is given by using a character string, the notification can be given by displaying, for example, "AI: ON" or "AI: Supported" instead of "AI is active". Similarly, the notification can be given by displaying, for example, "AI: OFF" or "AI: Not supported" instead of "AI is inactive". In addition, as illustrated in FIG. 11, the notification unit 65 can give the notification that the recognition process is functioning by adding a double-line frame 161 to the display 141 "normal observation mode" instead of the display 122 using the character string "AI is active". Further, as illustrated in FIG. 12, the notification unit 65 can give the notification that the recognition process is not functioning by, for example, adding a single-line frame 162 to display 143 "special observation mode" instead of the display 132 using the character string "AI is inactive".

Figure 13:
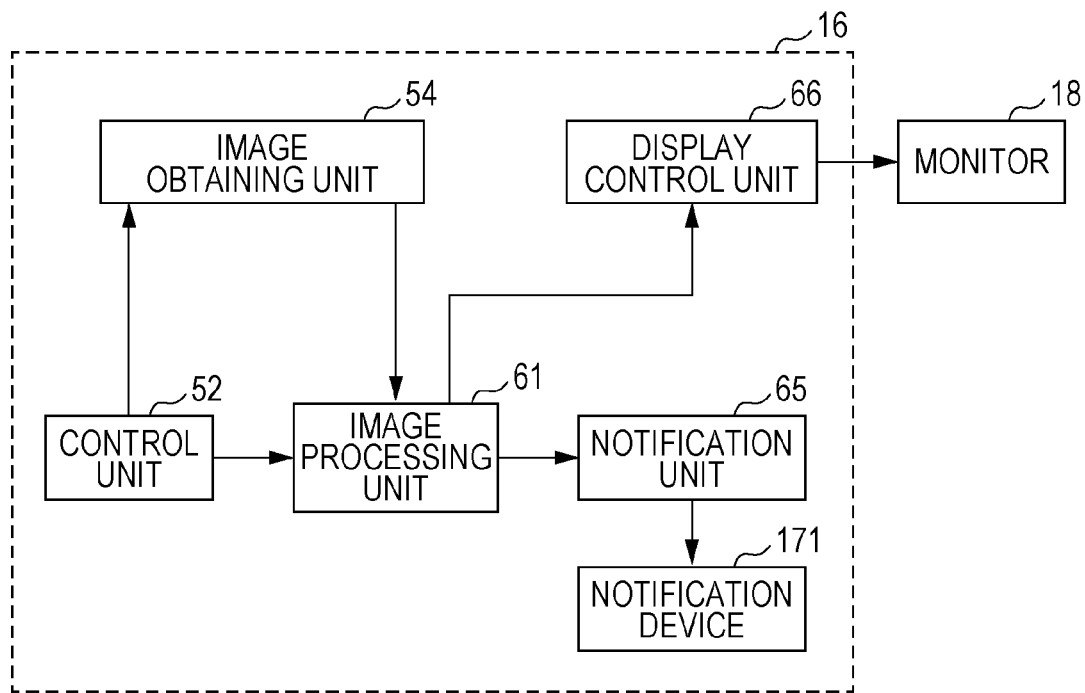
FIG. 13 is a block diagram of a processor device in a case of giving a notification of whether a recognition process functions with a method other than display on a monitor.

In the first embodiment described above, the notification unit 65 gives the notification of whether the recognition process functions by display on the screen of the monitor 18; however, in a case where the notification unit 65 gives the notification of whether the recognition process functions in a form other than display on the screen of the monitor 18, the processor device 16 can include a notification device 171 as illustrated in FIG. 13. The notification device 171 is, for example, a speaker that generates a sound or voice, an indicator formed of a light-emitting device, such as an LED, or a vibrating device, such as a motor or a piezoelectric element. In addition, the notification unit 65 can use, for example, a device included in the endoscope system 10 as the notification device 171. Further, the notification device 171 may be provided not in the processor device 16 but in the endoscope 12 or in the light source device 14.

Second Embodiment

In this embodiment, the endoscope system 10 has two types of operation modes, namely, an enlargement-observation mode in which the optical enlargement process and/or the electronic enlargement process is performed to allow enlargement observation of a photographic subject and a non-enlargement-observation mode in which the optical enlargement process and/or the electronic enlargement process is not used. In this case, the identification unit 73 can identify the type of image on the basis of whether or not the enlargement process is performed.

Figure 14:
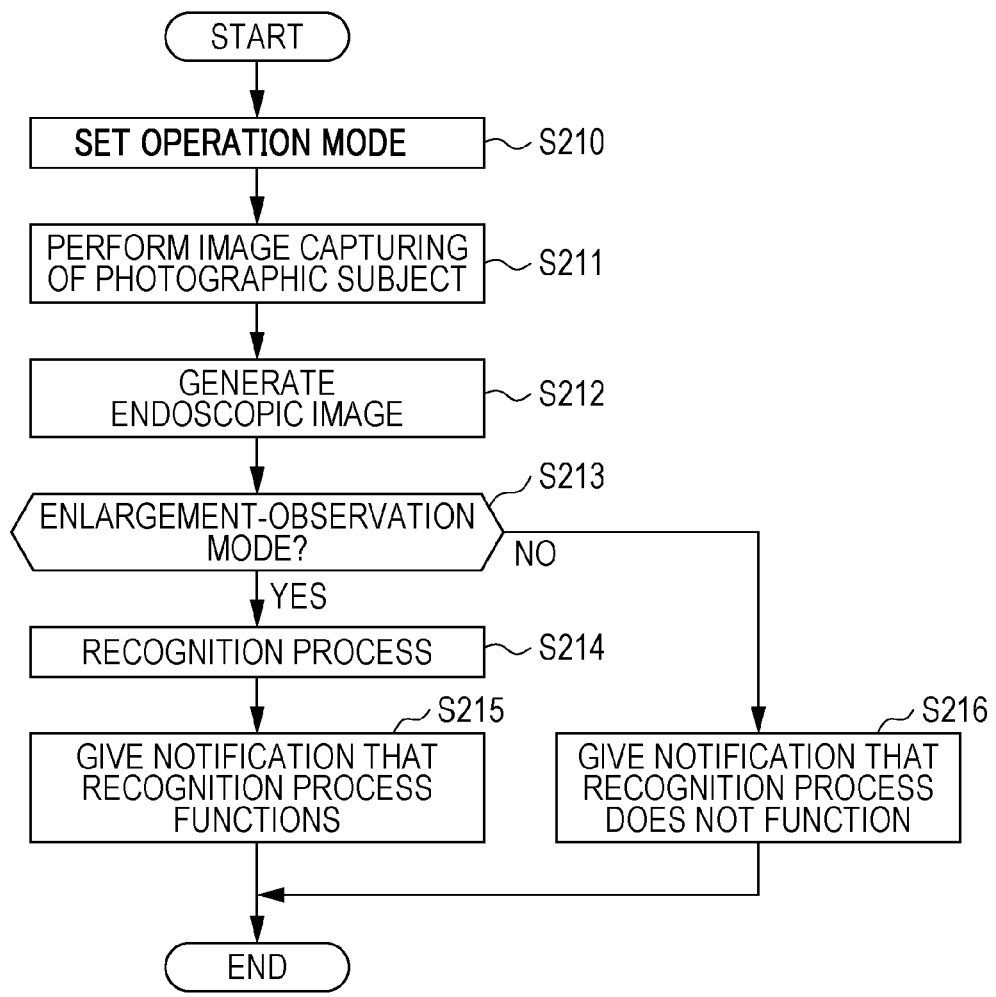
FIG. 14 is a flowchart of a second embodiment.

Specifically, as illustrated in FIG. 14, when a doctor or the like operates the mode switching operation part 13*b* to set the operation mode (step S210) and performs image capturing of a photographic subject (step S211), the image obtaining unit 54 obtains an endoscopic image, and the image generation unit 71 performs necessary image processing and generates an endoscopic image for display (step S212). These are the same as in the first embodiment.

Meanwhile, the identification unit 73 determines whether the operation mode is the enlargement-observation mode or the non-enlargement-observation mode (step S213) to thereby identify the type of image. For example, the identification unit 73 identifies an endoscopic image that is obtained in the enlargement-observation mode as an image for which the recognition process functions (YES in step S213). Then, the recognition unit 72 performs the recognition process for the endoscopic image obtained in the enlargement-observation mode (step S214), and the notification unit 65 gives a notification that the recognition process functions (step S215). The identification unit 73 identifies an endoscopic image obtained in the non-enlargement-observation mode as an image for which the recognition process does not function (NO in step S213). Then, the recognition unit 72 does not perform the recognition process for the endoscopic image obtained in the non-enlargement-observation mode, and the notification unit 65 gives a notification that the recognition process does not function (step S216). The method for notification is the same as in the first embodiment and the modifications.

According to the second embodiment described above, in each of the enlargement-observation mode and the non-enlargement-observation mode, both in a case where the result of the recognition process is displayed and in a case where the result of the recognition process is not displayed, a doctor or the like can correctly recognize whether the recognition process is functioning without incorrectly recognizing the result of performing the recognition process and the result of not performing the recognition process. As a consequence, it is possible to prevent wrong diagnoses.

In the flowchart illustrated in FIG. 14, the recognition process is performed in the case of the enlargement-observation mode. This is effective in a case where the recognition unit 72 is an AI that learns detection and/or determination of lesions or the like using endoscopic images that are subjected to the enlargement process. The endoscope system 10 can perform the recognition process in the case of the non-enlargement-observation mode. This is effective in a case where the recognition unit 72 is an AI that learns detection and/or determination of lesions or the like using endoscopic images that are not subjected to the enlargement process. That is, the second embodiment described above is effective in a case where the recognition unit 72 is an AI that learns detection and/or determination of lesions or the like using endoscopic images that are obtained in the enlargement-observation mode or in the non-enlargement-observation mode.

Note that the second embodiment described above can be combined with the first embodiment. For example, in a case where the operation mode is a combination of the normal observation mode and the enlargement-observation mode, a combination of the normal observation mode and the non-enlargement-observation mode, a combination of the special observation mode and the enlargement-observation mode, or a combination of the special observation mode and the non-enlargement-observation mode, it is possible to perform the recognition process and give a notification that the recognition process functions. Otherwise, it is possible to give a notification that the recognition process does not function without performing the recognition process.

Third Embodiment

In this embodiment, the endoscope system 10 has two types of operation modes, namely, a highlight mode in which the highlighting process is performed and a non-highlight mode in which the highlighting process is not performed. In this case, the identification unit 73 can identify the type of image on the basis of whether or not the highlighting process is performed.

Figure 15:
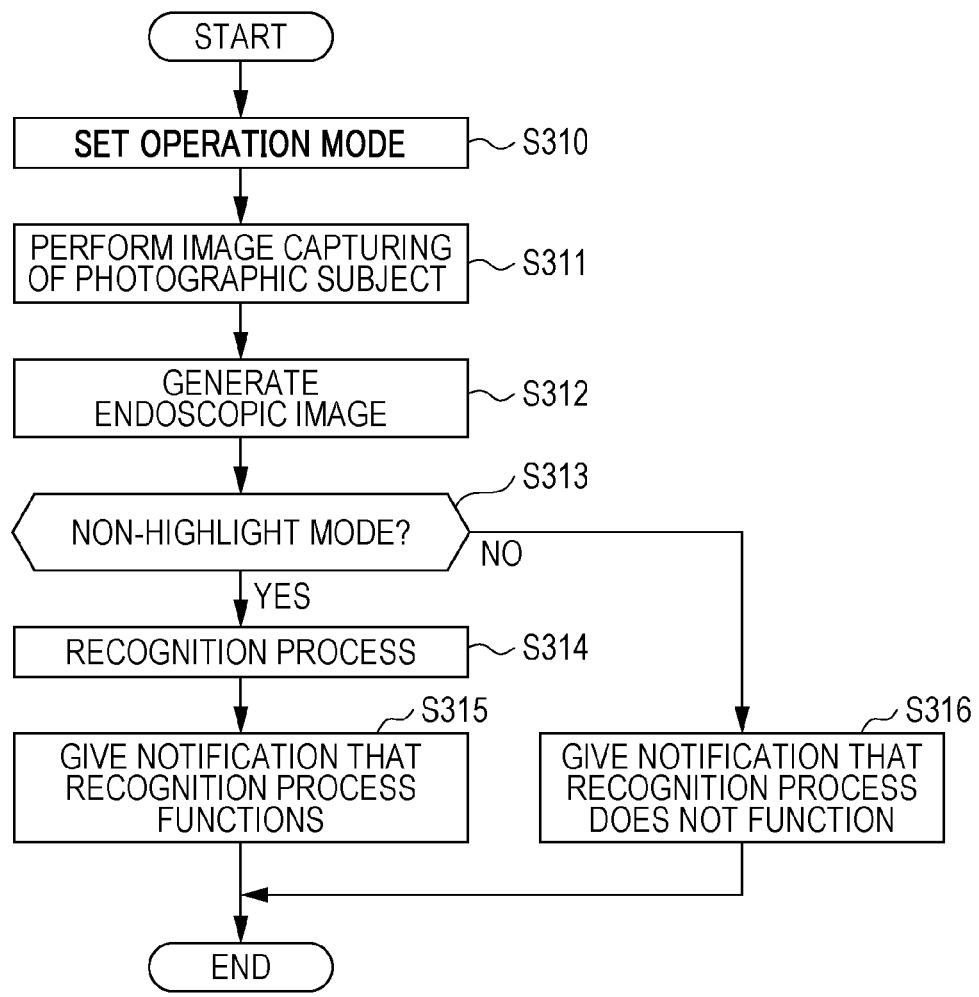
FIG. 15 is a flowchart of a third embodiment.

Specifically, as illustrated in FIG. 15, when a doctor or the like operates the mode switching operation part 13*b* to set the operation mode (step S310) and performs image capturing of a photographic subject (step S311), the image obtaining unit 54 obtains an endoscopic image, and the image generation unit 71 performs necessary image processing and generates an endoscopic image for display (step S312). These are the same as in the first embodiment.

Meanwhile, the identification unit 73 determines whether the operation mode is the highlight mode or the non-highlight mode (step S313) to thereby identify the type of image. For example, the identification unit 73 identifies an endoscopic image that is obtained in the non-highlight mode as an image for which the recognition process functions (YES in step S313). Then, the recognition unit 72 performs the recognition process for the endoscopic image obtained in the non-highlight mode (step S314), and the notification unit 65 gives a notification that the recognition process functions (step S315). The identification unit 73 identifies an endoscopic image obtained in the highlight mode as an image for which the recognition process does not function (NO in step S313). Then, the recognition unit 72 does not perform the recognition process for the endoscopic image obtained in the highlight mode, and the notification unit 65 gives a notification that the recognition process does not function (step S316). The method for notification is the same as in the first embodiment and the modifications.

According to the third embodiment described above, in each of the highlight mode and the non-highlight mode, both in the case where the result of the recognition process is displayed and in the case where the result of the recognition process is not displayed, a doctor or the like can correctly recognize whether the recognition process is functioning without incorrectly recognizing the result of performing the recognition process and the result of not performing the recognition process. As a consequence, it is possible to prevent wrong diagnoses.

In the flowchart illustrated in FIG. 15, the recognition process is performed in the case of the non-highlight mode. This is effective in a case where the recognition unit 72 is an AI that learns detection and/or determination of lesions or the like using endoscopic images that are not subjected to the highlighting process. The endoscope system 10 can perform the recognition process in the case of the highlight mode. This is effective in a case where the recognition unit 72 is an AI that learns detection and/or determination of lesions or the like using endoscopic images for which the highlighting process is performed for lesions or the like. That is, the third embodiment described above is effective in a case where the recognition unit 72 is an AI that learns detection and/or determination of lesions or the like using endoscopic images that are obtained in the highlight mode or in the non-highlight mode.

Note that the third embodiment described above can be combined with the first embodiment and/or the second embodiment. For example, in a case where the operation mode is a combination of the normal observation mode and the highlight mode, a combination of the normal observation mode and the non-highlight mode, a combination of the special observation mode and the highlight mode, or a combination of the special observation mode and the non-highlight mode, it is possible to perform the recognition process and give a notification that the recognition process functions. Otherwise, it is possible to give a notification that the recognition process does not function without performing the recognition process. The same applies to a case of a combination with the second embodiment or a case of a combination with the first embodiment and the second embodiment.

Fourth Embodiment

In this embodiment, use of a plurality endoscopes 12 of different models is allowed. In this case, the identification unit 73 can identify the type of image on the basis of the model of the endoscope 12.

Figure 16:
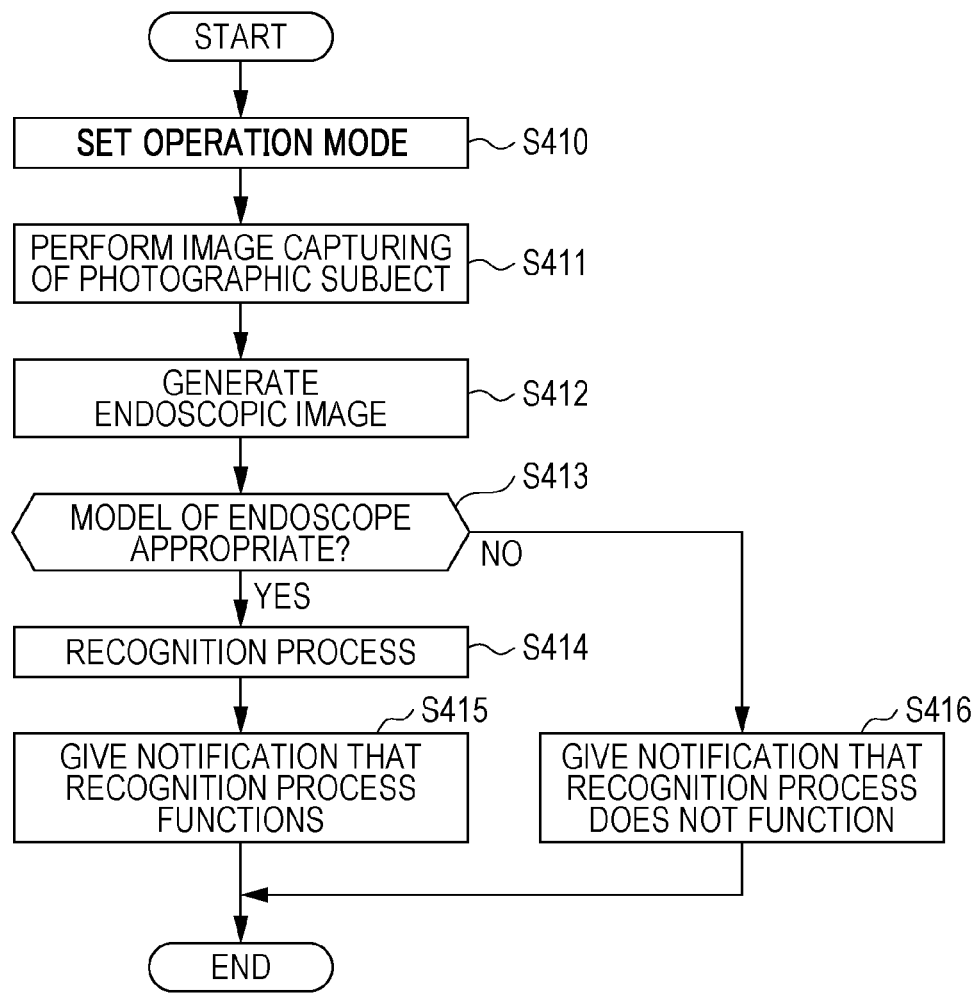
FIG. 16 is a flowchart of a fourth embodiment.

Specifically, as illustrated in FIG. 16, when a doctor or the like operates the mode switching operation part 13b to set the operation mode (step S410) and performs image capturing of a photographic subject (step S411), the image obtaining unit 54 obtains an endoscopic image, and the image generation unit 71 performs necessary image processing and generates an endoscopic image for display (step S412). These are the same as in the first embodiment.

Meanwhile, the identification unit 73 determines whether the model of the endoscope 12 in use is an appropriate one (step S413) to thereby identify the type of image. For example, the identification unit 73 identifies an endoscopic image that is obtained by using the endoscope 12 of a specific model as an image for which the recognition process functions (YES in step S413). Then, the recognition unit 72 performs the recognition process for the endoscopic image obtained by using the endoscope 12 of the specific model (step S414), and the notification unit 65 gives a notification that the recognition process functions (step S415). The identification unit 73 identifies an endoscopic image obtained by using the endoscope 12 of a model other than the specific model (hereinafter referred to as a non-specific model) as an image for which the recognition process does not function (NO in step S413). Then, the recognition unit 72 does not perform the recognition process for the endoscopic image obtained by using the endoscope 12 of the non-specific model, and the notification unit 65 gives a notification that the recognition process does not function (step S416). The method for notification is the same as in the first embodiment and the modifications.

According to the fourth embodiment described above, in each of the case where the endoscope 12 of the specific model is used and the case where the endoscope 12 of the non-specific model is used, both in the case where the result of the recognition process is displayed and in the case where the result of the recognition process is not displayed, a doctor or the like can correctly recognize whether the recognition process is functioning without incorrectly recognizing the result of performing the recognition process and the result of not performing the recognition process. As a consequence, it is possible to prevent wrong diagnoses.

The type of the image sensor 48 mounted in the endoscope 12 (for example, the characteristics of the color filters) differs depending on the model of the endoscope 12, and therefore, the characteristics of the obtained endoscopic image become different. For example, even in a case where image capturing of the same photographic subject is performed, for example, the color, brightness, or solution of the endoscopic image may be different depending on the model of the endoscope 12. The fourth embodiment described above is effective in a case where the recognition unit 72 learns detection and/or determination of lesions or the like using endoscopic images captured by using the endoscope 12 of the specific model. In a case where there are a plurality of types of endoscopes 12 with which images for which the recognition process functions can be obtained, the "endoscope 12 of the specific model" described above is a group that includes the plurality of types (models) of endoscopes 12.

Note that the fourth embodiment described above can be combined with the first embodiment, the second embodiment, and/or the third embodiment. For example, in a case where the operation mode is the normal observation mode and the endoscope 12 of the specific model is used, it is possible to perform the recognition process and give a notification that the recognition process functions. Otherwise, it is possible to give a notification that the recognition process does not function without performing the recognition process. The same applies to a case of a combination with the other embodiments.

Fifth Embodiment

Figure 17:
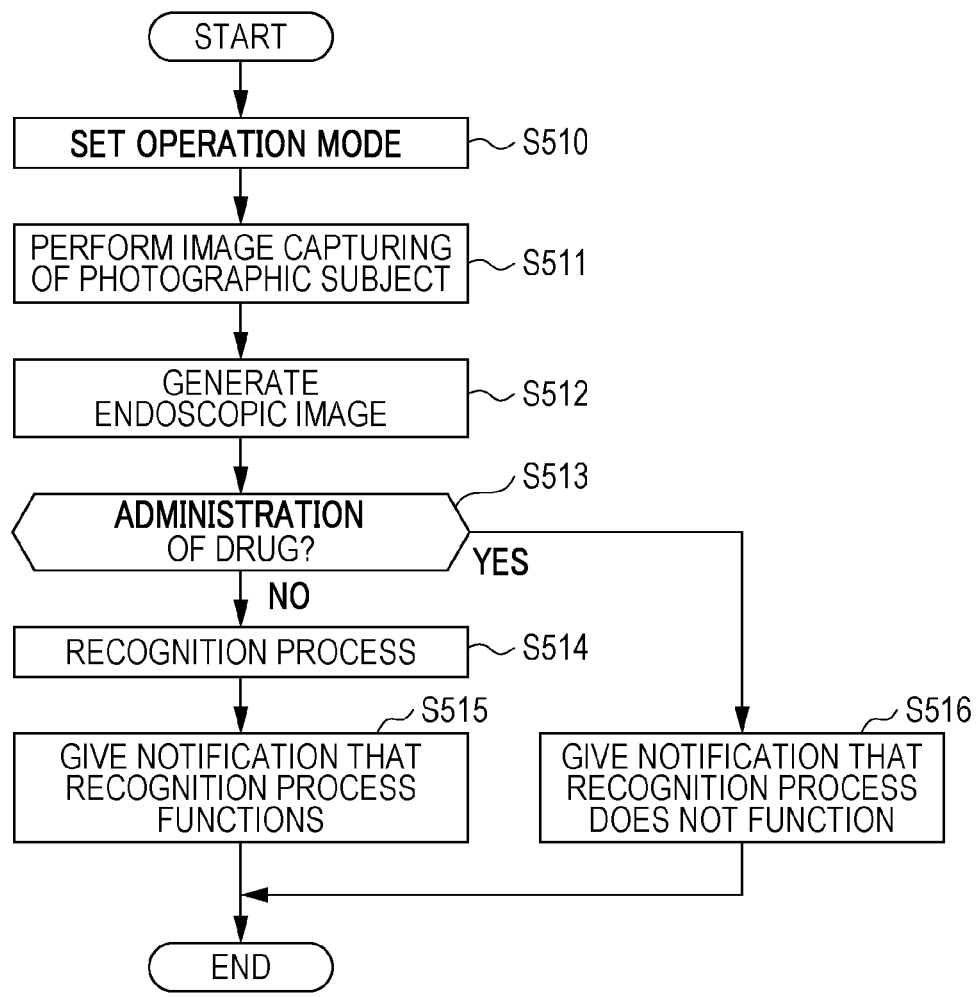
FIG. 17 is a flowchart of a fifth embodiment.

In a case where the identification unit 73 identifies the type of image on the basis of whether or not a drug is administered to the photographic subject, the endoscope system 10 operates as illustrated in FIG. 17. Specifically, when a doctor or the like operates the mode switching operation part 13b to set the operation mode (step S510) and performs image capturing of a photographic subject (step S511), the image obtaining unit 54 obtains an endoscopic image, and the image generation unit 71 performs necessary image processing and generates an endoscopic image for display (step S512). These are the same as in the first embodiment.

Meanwhile, the identification unit 73 determines whether or not a drug is administered to the photographic subject (step S513) to thereby identify the type of image. For example, the identification unit 73 identifies an endoscopic image that is obtained without administration of a drug to the photographic subject as an image for which the recognition process functions (YES in step S513). Then, the recognition unit 72 performs the recognition process for the endoscopic image obtained by image capturing of the photographic subject to which a drug is not administered (step S514), and the notification unit 65 gives a notification that the recognition process functions (step S515). The identification unit 73 identifies an endoscopic image obtained by image capturing of the photographic subject to which a drug is administered as an image for which the recognition process does not function (NO in step S513). Then, the recognition unit 72 does not perform the recognition process for the endoscopic image obtained by image capturing of the photographic subject to which a drug is administered, and the notification unit 65 gives a notification that the recognition process does not function (step S516). The method for notification is the same as in the first embodiment and the modifications.

According to the fifth embodiment described above, in each of the case where a drug is administered to the photographic subject and the case where the a drug is not administered to the photographic subject, both in the case where the result of the recognition process is displayed and in the case where the result of the recognition process is not displayed, a doctor or the like can correctly recognize whether the recognition process is functioning without incorrectly recognizing the result of performing the recognition process and the result of not performing the recognition process.

Note that in the fifth embodiment described above, the recognition unit 72 performs the recognition process in a case where a drug is not administered to the photographic subject. This is effective in a case where the recognition unit 72 is an AI that learns detection and/or determination of lesions or the like using endoscopic images of photographic subjects to which a drug is not administered. The endoscope system 10 can perform the recognition process in a case where a specific drug is administered to the photographic subject. This is effective in a case where the recognition unit 72 learns detection and/or determination of lesions or the like using endoscopic images of photographic subjects to which the specific drug is administered. In this case, the identification unit 73 can identify the type of drug administered to the photographic subject with reference to setting information or by analyzing the endoscopic image to thereby identify the type of image.

Note that the fifth embodiment described above can be combined with the first embodiment, the second embodiment, the third embodiment, the fourth embodiment, or a plurality of embodiments among the first to fourth embodiments. For example, in a case where the operation mode is the normal observation mode and a drug is not administered, the endoscope system 10 can perform the recognition process and give a notification that the recognition process functions. Otherwise, the endoscope system 10 can give a notification that the recognition process does not function without performing the recognition process. The same applies to the other combinations.

Sixth Embodiment

Figure 18:
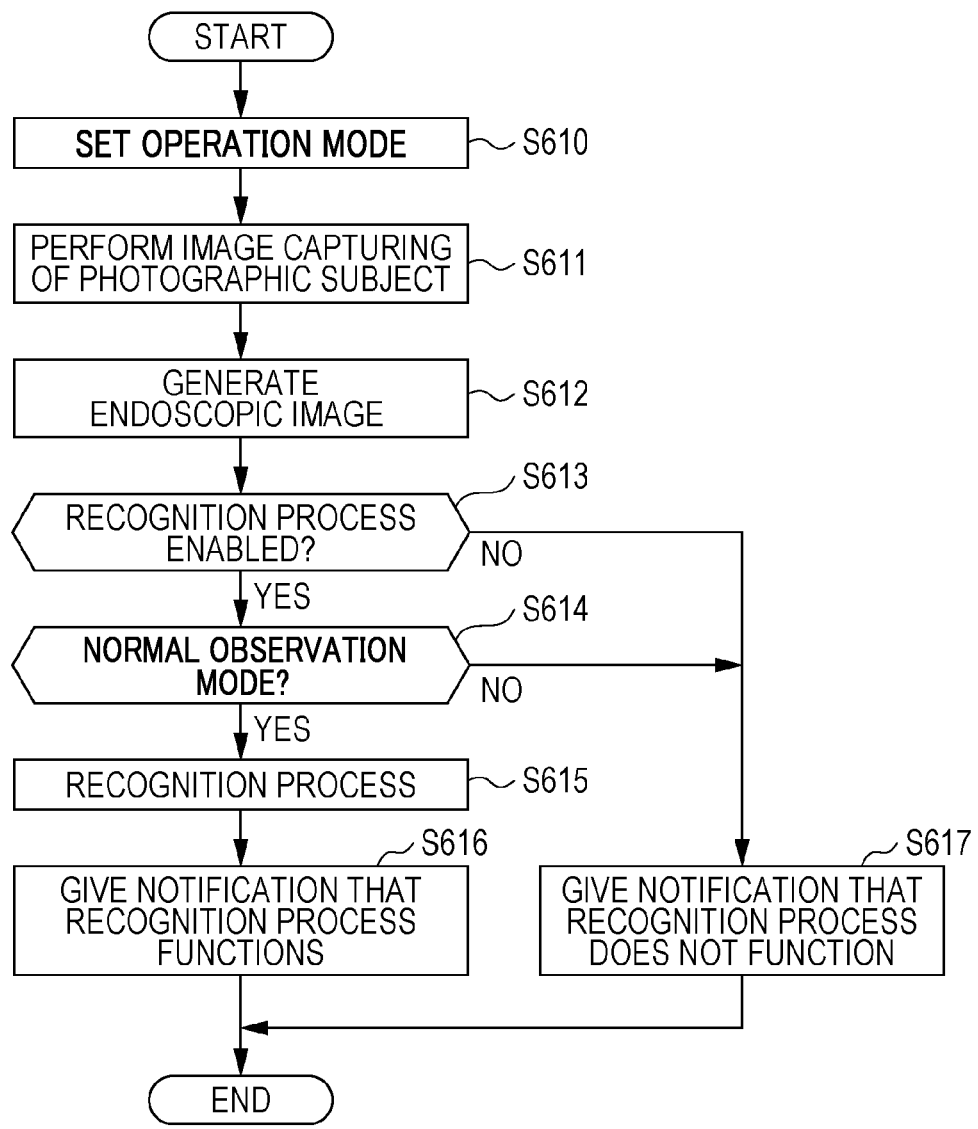
FIG. 18 is a flowchart of a sixth embodiment.

In the first embodiment and so on, the identification unit 73 automatically activates or inactivates the recognition unit 72; however, in the endoscope system 10, a doctor or the like can manually perform setting to enable the recognition process or perform setting to disable the recognition process instead of automatic activation or inactivation of the recognition unit 72. In this case, as illustrated in FIG. 18, when a doctor or the like operates the mode switching operation part 13b to set the operation mode (step S610) and performs image capturing of a photographic subject (step S611), the image obtaining unit 54 obtains an endoscopic image, and the image generation unit 71 performs necessary image processing and generates an endoscopic image for display (step S612). These are the same as in the first embodiment.

Meanwhile, the identification unit 73 determines whether the recognition process is enabled or disabled with reference to setting information (step S613) and determines the operation mode (step S614) to thereby identify the type of image. In a case where the recognition process is enabled by manual setting (YES in step S613) and if the operation mode is the normal observation mode (YES in step S614), the recognition unit 72 performs the recognition process (step S615), and the notification unit 65 gives a notification that the recognition process functions (step S616). In a case where the recognition process is disabled by manual setting (NO in step S613) or in a case where the operation mode is the special observation mode (NO in step S614), the recognition unit 72 does not perform the recognition process, and the notification unit 65 gives a notification that the recognition process does not function (step S617). The method for notification is the same as in the first embodiment and the modifications.

According to the sixth embodiment described above, the notification unit 65 appropriately gives a notification of whether the recognition process functions, and therefore, both in the case where the result of the recognition process is displayed and in the case where the result of the recognition process is not displayed, a doctor or the like can correctly recognize whether the recognition process is functioning without incorrectly recognizing the result of performing the recognition process and the result of not performing the recognition process. For example, even in a case where a doctor or the like does not remember having disabled the recognition process by manual setting, the notification unit 65 gives a notification that the recognition process does not function, and therefore, the doctor or the like can correctly recognize that the result of the recognition process is not displayed because the recognition process is not functioning.

The sixth embodiment can be implemented in combination with the first embodiment, the second embodiment, the third embodiment, the fourth embodiment, the fifth embodiment, or a plurality of embodiments among the first to fifth embodiments as desired.

Seventh Embodiment

In the first embodiment and so on described above, the identification unit 73 automatically activates or inactivates the recognition unit 72, and therefore, the notification unit 65 gives a notification stating whether the recognition process functions. In a case where the identification unit 73 does not automatically activate or inactivate the recognition unit 72, it is preferable that the notification unit 65 give a notification of whether the recognition process functions in a form that differs depending on whether the recognition unit 72 is active or the recognition unit 72 is inactive.

Figures 19, 20:
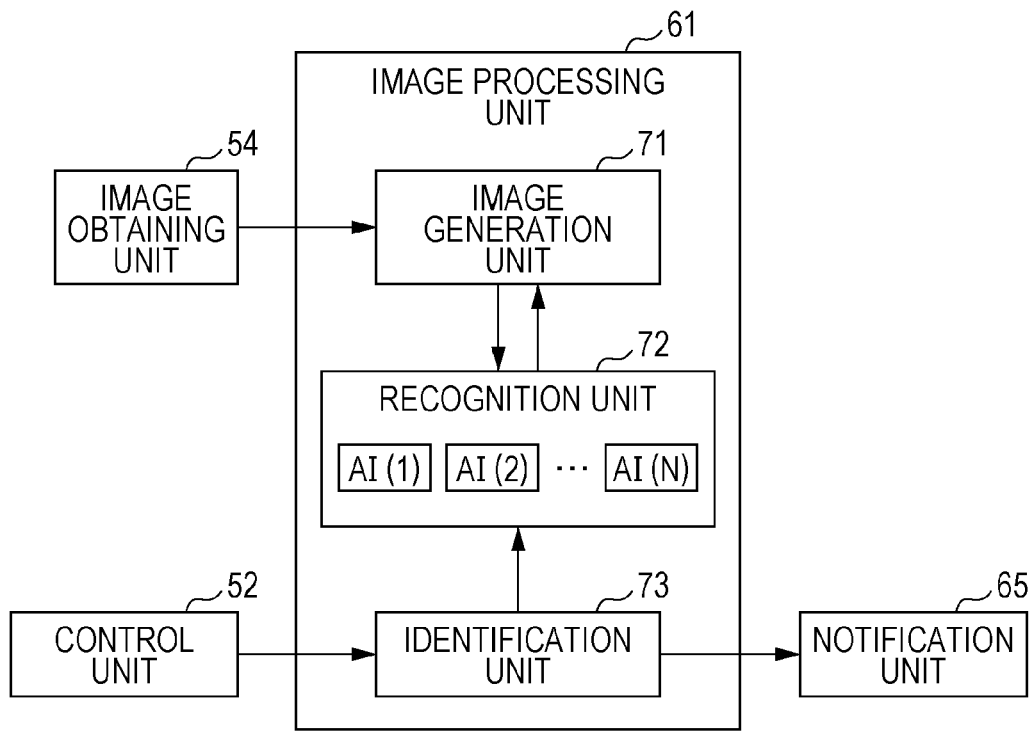
FIG. 19 is an explanatory diagram illustrating four types of notification forms.
FIG. 20 is a block diagram of the image processing unit in a case where a recognition unit includes a plurality of AIs.

Specifically, as illustrated in FIG. 19, in a case where the recognition unit 72 is active, and accordingly, the recognition process is "enabled" and where, for example, the operation mode is a mode in which an image for which the recognition process functions is obtained (recognition process: possible), the notification unit 65 gives a notification of whether the recognition process functions in a first notification form. The first notification form is, for example, the display 122 "AI is active". On the other hand, in a case where the recognition unit 72 is inactive (is not yet activated), and accordingly, the recognition process is "disabled" and where, for example, the operation mode is a mode in which an image for which the recognition process functions is obtained (recognition process: possible), the notification unit 65 gives a notification of whether the recognition process functions in a second notification form. The second notification form is, for example, display of "AI is not yet activated", "recognition process is possible with AI", or "AI is not activated and AI is inactive accordingly".

In a case where the recognition unit 72 is active, and accordingly, the recognition process is "enabled" and where, for example, the operation mode is a mode in which an image for which the recognition process does not function is obtained (recognition process: not possible), the notification unit 65 gives a notification of whether the recognition process functions in a third notification form. The third notification form is, for example, display of "recognition process error", "AI is unable to handle", or "AI is unable to handle and AI is inactive accordingly". In a case where the recognition unit 72 is inactive, and accordingly, the recognition process is "disabled" and where, for example, the operation mode is a mode in which an image for which the recognition process does not function is obtained (recognition process: not possible), the notification unit 65 gives a notification of whether the recognition process functions in a fourth notification form. The fourth notification form is, for example, the display 132 "AI is inactive".

As in the seventh embodiment described above, when the notification unit 65 gives a notification in a form that differs depending on whether the recognition unit 72 is active or the recognition unit 72 is inactive, a doctor or the like can accurately grasp the operation state of the recognition unit 72 and the result of the recognition process in detail without incorrect recognition. Further, for example, when the doctor or the like sees the content of the notification in the second notification form, it is obvious to the doctor or the like that the recognition process can be performed. Therefore, even in a case where the doctor or the like has manually disabled the recognition process, the doctor or the like can easily enable the recognition process to receive support of the endoscope system 10.

Note that in the first embodiment and so on, the notification unit 65 gives a notification in the first notification form or in the fourth notification form. In the seventh embodiment described above, all of the first notification form, the second notification form, the third notification form, and the fourth notification form are different forms of display; however, the seventh embodiment needs to include one or more patterns in which a notification is given in a form that differs depending on whether the recognition unit 72 is active or the recognition unit 72 is inactive, and two or more forms among the first notification form, the second notification form, the third notification form, and the fourth notification form may be the same forms of display. For example, the second notification form and/or the third notification form may be the same as the fourth notification form, that is, the display 132 "AI is inactive". In this case, at least the first notification form and the second notification form are different, and therefore, a doctor or the like can accurately grasp the operation state of the recognition unit 72 and the result of the recognition process in detail without incorrect recognition.

Eighth Embodiment

In the first embodiment and so on, the recognition unit 72 is an AI that performs the recognition process for detecting lesions or the like; however, the recognition unit 72 can be formed of a plurality of AIs, such as AI(1), AI(2), ..., AI(N) illustrated in FIG. 20, that function (perform recognition processes) for different types of images. A(1) is, for example, an AI that learns detection of lesions or the like using endoscopic images that are obtained by performing enlarging image capturing of photographic subjects to which a drug is not administered in the normal observation mode. AI(2) is, for example, an AI that learns determination of lesions or the like using endoscopic images obtained under conditions the same as the conditions for AI(1). AI(3) not illustrated is, for example, an AI that learns detection of lesions or the like using endoscopic images that are obtained by performing enlarging image capturing of photographic subjects to which a drug is not administered in the special observation mode. The other AIs are similarly obtained through respective learning.

As described above, in a case where the recognition unit 72 includes a plurality of AIs that perform different recognition processes, the identification unit 73 identifies the type of image by determining whether at least one of the plurality of AIs functions. The notification unit 65 gives, for each of the plurality of AIs, a notification of whether the recognition process functions. Accordingly, even in the case where the recognition unit 72 includes a plurality of AIs, for each of the AIs, a notification of whether the recognition process functions can be accurately given. Note that the notification unit 65 can give a notification that the recognition process functions in a case where at least one of the plurality of AIs functions. In this case, a notification that the recognition process functions can be given more briefly than in a case where a notification of whether the recognition process functions is given for each of the AIs.

Figure 21:
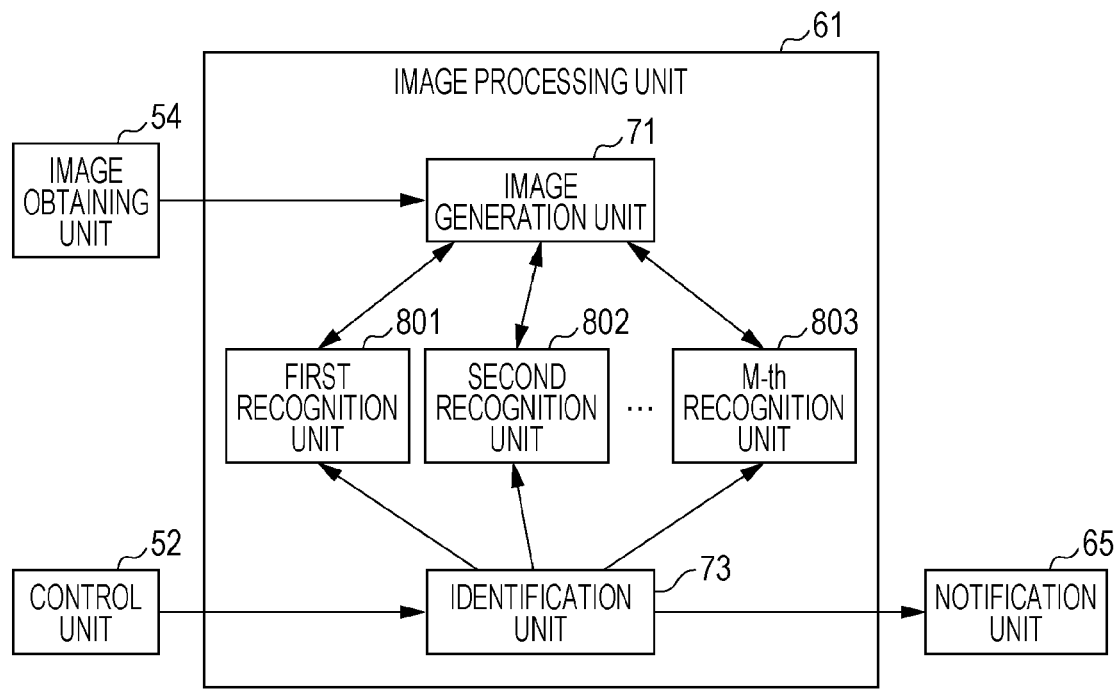
FIG. 21 is a block diagram of the image processing unit in a case where the image processing unit has a plurality of recognition units.

In the eighth embodiment described above, one recognition unit 72 includes a plurality of AIs; however, the same applies to a case where the image processing unit 61 includes a plurality of recognition units, such as a first recognition unit 801, a second recognition unit 802, ..., an M-th recognition unit 803, that function (perform recognition processes) for different types of images instead of the recognition unit 72, as illustrated in FIG. 21. That is, in a case where the image processing unit 61 includes a plurality of recognition units (the first recognition unit 801, the second recognition unit 802, and so on) instead of the recognition unit 72, the notification unit 65 gives, for each of the plurality of recognition units, a notification of whether the recognition process functions. Accordingly, even in the case where the image processing unit 61 includes a plurality of recognition units instead of the recognition unit 72, for each of the recognition units, a notification of whether the recognition process functions can be accurately given. Note that the notification unit 65 may give a notification that the recognition process functions in a case where at least one of the plurality of recognition units, namely, the first recognition unit 801, the second recognition unit 802, and so on, functions. In this case, a notification that the recognition process functions can be given more briefly than in a case where a notification of whether the recognition process functions is given for each of the recognition units.

Figure 22:
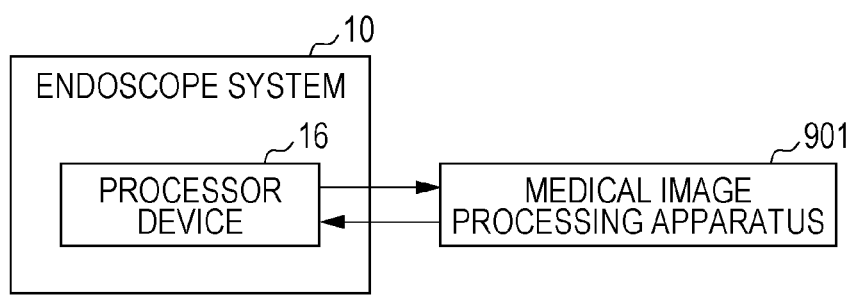
FIG. 22 is an explanatory diagram illustrating a medical image processing apparatus.
Figure 23:
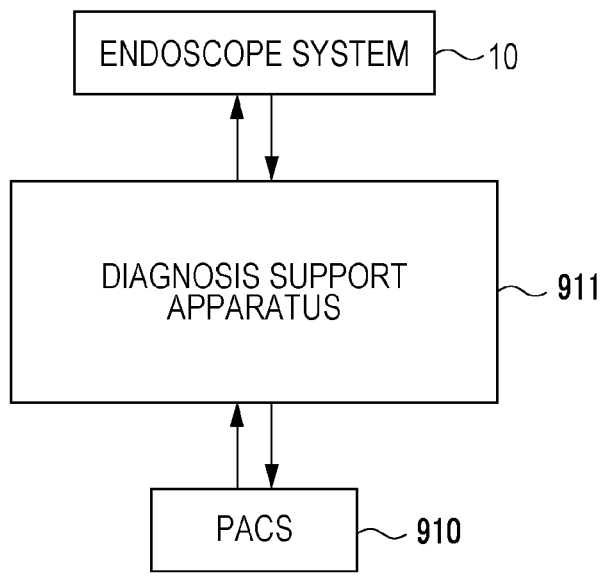
FIG. 23 is an explanatory diagram illustrating a diagnosis support apparatus.
Figure 24:
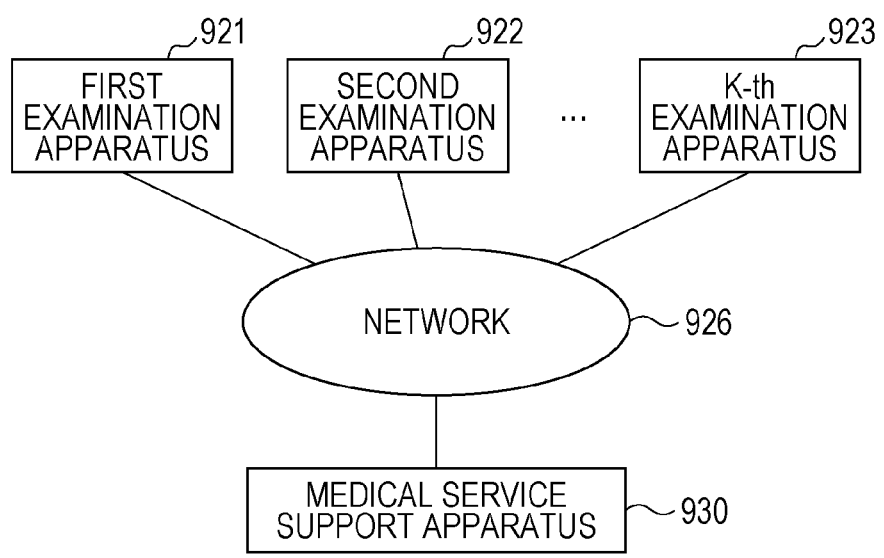
FIG. 24 is an explanatory diagram illustrating a medical service support apparatus.

As illustrated in FIG. 22, the recognition unit 72, the identification unit 73, and/or the notification unit 65 can be provided in, for example, a medical image processing apparatus 901 that communicates with the processor device 16 to cooperate with the endoscope system 10. As illustrated in FIG. 23, the recognition unit 72, the identification unit 73, and/or the notification unit 65 can be provided in, for example, a diagnosis support apparatus 911 that obtains directly from the endoscope system 10 (including one that does not have the notification unit 65 and so on) or indirectly from a PACS (Picture Archiving and Communication Systems) 910, raw images captured by the endoscope 12. Further, as illustrated in FIG. 24, the recognition unit 72, the identification unit 73, and/or the notification unit 65 can be provided in a medical service support apparatus 930 that is connected, via a network 926, to various examination apparatuses, such as a first examination apparatus 921, a second examination apparatus 922, ..., a K-th examination apparatus 923, that include the endoscope system 10.

That is, the present invention includes a medical image processing apparatus including an identification unit that identifies the type of an image obtained by image capturing of a photographic subject, a recognition unit that performs a recognition process of recognizing the photographic subject by using the image, and a notification unit that gives a notification of whether the recognition process functions for the image of a specific type identified by the identification unit, and an operation method for the medical image processing apparatus. Further, the present invention includes a diagnosis support apparatus including an identification unit that identifies the type of an image obtained by image capturing of a photographic subject, a recognition unit that performs a recognition process of recognizing the photographic subject by using the image, and a notification unit that gives a notification of whether the recognition process functions for the image of a specific type identified by the identification unit, and an operation method for the diagnosis support apparatus. Similarly, the present invention includes a medical service support apparatus including an identification unit that identifies the type of an image obtained by image capturing of a photographic subject, a recognition unit that performs a recognition process of recognizing the photographic subject by using the image, and a notification unit that gives a notification of whether the recognition process functions for the image of a specific type identified by the identification unit, and an operation method for the medical service support apparatus.

The present invention includes an operation method for an endoscope system, the operation method including a step of identifying, by an identification unit, the type of an image obtained by image capturing of a photographic subject, a step of performing, by a recognition unit, a recognition process of recognizing the photographic subject by using the image, and a step of giving, by a notification unit, a notification of whether the recognition process functions for the image of a specific type identified by the identification unit. Further, the present invention includes a processor device including an identification unit that identifies the type of an image obtained by image capturing of a photographic subject, a recognition unit that performs a recognition process of recognizing the photographic subject by using the image, and a notification unit that gives a notification of whether the recognition process functions for the image of a specific type identified by the identification unit, and an operation method for the processor device.

Note that as the endoscope 12, a capsule endoscope can be used. In this case, the light source device 14 and part of the processor device 16 can be mounted in the capsule endoscope.

In the above embodiments, the hardware configuration of the processing units that perform various types of processing of, for example, the recognition unit 72, the identification unit 73, and the notification unit 65 is implemented as various processors as described below. The various processors include a CPU (central processing unit), which is a general-purpose processor executing software (program) to function as various processing units, a GPU (graphical processing unit), a programmable logic device (PLD), such as an FPGA (field-programmable gate array), which is a processor having a circuit configuration that is changeable after manufacture, and a dedicated electric circuit, which is a processor having a circuit configuration specifically designed to perform various types of processing.

One processing unit may be configured as one of the various processors or a combination of two or more processors of the same type or different types (for example, a plurality of FPGAs, a combination of a CPU and an FPGA, or a combination of a CPU and a GPU). Further, a plurality of processing units may be configured as one processor. As the first example of configuring a plurality of processing units as one processor, a form is possible where one or more CPUs and software are combined to configure one processor, and the processor functions as the plurality of processing units, a representative example of which is a computer, such as a client or a server. As the second example thereof, a form is possible where a processor is used in which the functions of the entire system including the plurality of processing units are implemented as one IC (integrated circuit) chip, a representative example of which is a system on chip (SoC). As described above, regarding the hardware configuration, the various processing units are configured by using one or more of the various processors described above.

Further, the hardware configuration of the various processors is more specifically an electric circuit (circuitry) in a form in which circuit elements, such as semiconductor elements, are combined.

Note that the present invention can be used in, for example, a system or an apparatus that obtains medical images (including moving images) other than endoscopic images as well as an endoscope system that, for example, obtains endoscopic images, a processor device, and other related apparatuses. For example, the present invention is applicable to ultrasonic examination apparatuses, X-ray imaging apparatuses (including CT (computed tomography) examination apparatuses and mammography apparatuses), and MRI (magnetic resonance imaging) apparatuses.

REFERENCE SIGNS LIST 10 endoscope system
12 endoscope
12a insertion part
12b operation part
12c bending part
12d tip part
12e angle knob
13a zoom operation part
13b mode switching operation part
14 light source device
16 processor device
18 monitor
19 console
20 light source unit
22 light source control unit
30a illumination optical system
30b imaging optical system
45 illumination lens
46 object lens
47 zoom lens
48 image sensor
52 control unit
54 image obtaining unit
56 DSP
58 noise reduction unit
59 conversion unit
61 image processing unit
65 notification unit
66 display control unit
71 image generation unit
72 recognition unit
73 identification unit
121, 124 normal observation image
122 display indicating that recognition process functions
131 special observation image
132 display indicating that recognition process does not function 141 display of normal observation mode
143 display of special observation mode
151 icon indicating that AI is active
152 icon indicating that AI is inactive
161 double-line frame
162 single-line frame
171 notification device
801 first recognition unit
802 second recognition unit
803 M-th recognition unit
901 medical image processing apparatus
910 PACS
911 diagnosis support apparatus
921 first examination apparatus
922 second examination apparatus
923 K-th examination apparatus
926 network
930 medical service support apparatus
S110 to S617 operation steps

What is claimed is:

1. An endoscope system comprising:
one or more processors configured to function as:
an identification unit that identifies a type of an image obtained by capturing a photographic subject;
a recognition unit that performs a recognition process of recognizing the photographic subject by using the image; and
a notification unit that gives a notification of whether the recognition process functions or not for the image identified by the identification unit,
wherein the identification unit identifies the type of the image according to an operation mode, a model of an endoscope used in capturing the photographic subject, or whether or not a drug is administered to the photographic subject,
wherein the identification unit identifies the type of the image by acquiring setting information of the operation mode, or information of the model of the endoscope used in capturing the photographic subject or whether or not the drug is administered to the photographic subject.

2. The endoscope system according to claim 1, wherein the identification unit identifies the type of the image according to the operation mode is determined on the basis of at least one of a type of illumination light used in capturing the photographic subject, whether or not an optical enlargement process is performed, or whether or not a specific image processing is performed.

3. The endoscope system according to claim 1, wherein the notification unit gives the notification of whether the recognition process functions at least in a case where the type of the image switches.

4. The endoscope system according to claim 1, wherein the notification unit gives the notification of whether the recognition process functions in a form that differs depending on whether the recognition unit is active or the recognition unit is inactive.

5. The endoscope system according to claim 1, wherein the recognition unit is automatically activated in a case where the type of the image is a type for which the recognition process functions, and the recognition unit is automatically inactivated in a case where the type of the image is a type for which the recognition process does not function.

6. The endoscope system according to claim 1, wherein the recognition unit recognizes presence or absence of a lesion or a potential lesion of the photographic subject.

7. The endoscope system according to claim 1, wherein the recognition unit recognizes a type or a degree of progression of a lesion or a potential lesion of the photographic subject.

8. The endoscope system according to claim 1, wherein the recognition unit is an artificial intelligence having a learning function.

9. The endoscope system according to claim 1, wherein in a case where the endoscope system has a plurality of recognition units that function for different types of images, each of the plurality of recognition units being the recognition unit, the notification unit gives, for each of the recognition units, the notification of whether the recognition process functions.

10. The endoscope system according to claim 1, wherein the notification is a notification whether the recognition process is active or inactive.

11. The endoscope system according to claim 1, wherein the operation mode is determined based on a type of illumination light used in capturing the photographic subject.

12. The endoscope system according to claim 1, wherein the one or more processors include an artificial intelligence as the recognition unit.

13. The endoscope system according to claim 1, wherein the notification unit further notifies the operation mode set by a user among a plurality of operation modes which use different types of illumination light each other.

14. The endoscope system according to claim 1, wherein the one or more processors are configured not to perform the recognition process in a case in which the operation mode set by a user between at least a first mode and a second mode is the second mode.

15. The endoscope system according to claim 14, wherein an accuracy of the recognition process based on an image of the second mode is lower than an accuracy of the recognition process based on an image of the first mode.

16. The endoscope system according to claim 14, wherein the one or more processors are configured to use white light in the first mode, and configured to use, in the second mode, illumination light containing more blue or violet components than the white light.

17. The endoscope system according to claim 16, wherein the one or more processors are configured to use the illumination light including more blue or violet components than the white light to facilitate observation of a blood vessel in the second mode.

18. The endoscope system according to claim 1, wherein the identification unit identifies the type of the image according to the operation mode on the basis of the type of illumination light used in capturing the photographic subject,
the recognition unit is automatically activated in a case where the type of illumination light is a first illumination light, and the recognition unit is automatically inactivated in a case where the type of illumination light is a second illumination light that contains more blue or violet components than the first illumination light,
the recognition unit recognizes presence or absence of a lesion or a potential lesion of the photographic subject and
the notification unit is configured to give the notification whether the recognition process is active or inactive by displaying on a screen.

19. An operation method of an endoscope system, the operation method comprising:

an identification step of identifying a type of an image obtained by capturing a photographic subject;

a recognition step of performing a recognition process of recognizing the photographic subject by using the image; and a notification step of giving a notification of whether or not the recognition process functions for the image identified by the identification step, wherein the identification step identifies the type of the image according to an operation mode, a model of an endoscope used in capturing the photographic subject, or whether or not a drug is administered to the photographic subject, wherein the identification step identifies the type of the image by acquiring setting information of the operation mode, or information of the model of the endoscope used in capturing the photographic subject or whether or not the drug is administered to the photographic subject.

20. The operation method according to claim 19, wherein the identification step identifies the type of the image according to the operation mode is determined on the basis of at least one of a type of illumination light used in capturing the photographic subject, whether or not an optical enlargement process is performed, or whether or not a specific image processing is performed.

21. The operation method according to claim 19, wherein the notification step gives the notification of whether the recognition process functions at least in a case where the type of the image switches.

22. The operation method according to claim 19, wherein the notification step gives the notification of whether the recognition process functions in a form that differs depending on whether the recognition step is active or the recognition step is inactive.

23. The operation method according to claim 19, wherein the recognition step is automatically activated in a case where the type of the image is a type for which the recognition process functions, and the recognition step is automatically inactivated in a case where the type of the image is a type for which the recognition process does not function.

24. The operation method according to claim 19, wherein the recognition step recognizes presence or absence of a lesion or a potential lesion of the photographic subject.

25. The operation method according to claim 19, wherein the recognition step recognizes a type or a degree of progression of a lesion or a potential lesion of the photographic subject.

26. The operation method according to claim 19, wherein the recognition step is performed by an artificial intelligence having a learning function.

27. The operation method according to claim 19, wherein in a case where the recognition step is performed by a plurality of recognition units that function for different types of images, the notification step gives, for each of the recognition units, the notification of whether the recognition process functions.

28. The operation method according to claim 19, wherein the notification is a notification whether the recognition process is active or inactive.

29. The operation method according to claim 19, wherein the operation mode is determined based on a type of illumination light used in capturing the photographic subject.

30. The operation method according to claim 19, wherein the notification step further notifies the operation mode set by a user among a plurality of operation modes which use different types of illumination light each other.

31. The operation method according to claim 19, wherein the recognition process is not performed in a case in which the operation mode set by a user between at least a first mode and a second mode is the second mode.

32. The operation method according to claim 31, wherein an accuracy of the recognition process based on an image of the second mode is lower than an accuracy of the recognition process based on an image of the first mode.

33. The operation method according to claim 31, wherein white light is used in the first mode, and illumination light containing more blue or violet components than the white light is used in the second mode.

34. The operation method according to claim 33, wherein, in the second mode, the illumination light including more blue or violet components than the white light is used to facilitate observation of a blood vessel.

35. The operation method according to claim 19, wherein the identification step identifies the type of the image according to the operation mode on the basis of at least one of a type of illumination light used in capturing the photographic subject, the recognition step is automatically activated in a case where the type of illumination light is a first illumination light, and the recognition step is automatically inactivated in a case where the type of illumination light is a second illumination light that contains more blue or violet components than the first illumination light, the recognition step recognizes presence or absence of a lesion or a potential lesion of the photographic subject, and the notification unit is configured to give the notification whether the recognition process is active or inactive by displaying on a screen.

* * * * *